United States Patent
Hung et al.

(10) Patent No.: US 6,172,212 B1
(45) Date of Patent: *Jan. 9, 2001

(54) PEA3 IS A TUMOR SUPPRESSOR

(75) Inventors: Mien-Chie Hung; Xiangming Xing, both of Houston, TX (US)

(73) Assignee: Board of Regents, The University of Texas System, Austin, TX (US)

( * ) Notice: Under 35 U.S.C. 154(b), the term of this patent shall be extended for 0 days.

This patent is subject to a terminal disclaimer.

(21) Appl. No.: 09/303,268

(22) Filed: Apr. 30, 1999

Related U.S. Application Data

(63) Continuation of application No. 08/780,835, filed on Jan. 10, 1997, now Pat. No. 5,922,688.

(51) Int. Cl.$^7$ .................. C07H 21/04; A61K 9/127; C12N 7/00; C12N 15/00; G01N 33/92
(52) U.S. Cl. .................. 536/23.5; 424/450; 424/93.1; 424/93.2; 435/235.1; 435/320.1; 436/71; 530/350; 514/44
(58) Field of Search .................. 514/44, 2; 435/320.1, 435/172.3, 325, 375, 975, 235.1; 424/93.2, 450; 436/71; 536/23.5; 530/350

(56) References Cited

U.S. PATENT DOCUMENTS 5,776,743  7/1998 Frisch .................. 435/6

FOREIGN PATENT DOCUMENTS

WO 95/21253  8/1995 (WO).

OTHER PUBLICATIONS

Chang et al., "ETS and OB2–1 factors mediate transcriptional overexpression of HER2/neu", *Proceedings of the American Association for Cancer Research* 36:532, Abstract #3167, 1995.

Dialog on–line search performed Jul. 15, 1996.

Galang, et al., "Oncogenic Neu/Erb–B–2 Increases Ets, AP–1, and NF–κB–dependent Gene Expression, and Inhibiting Ets Activation Blocks Neu–mediated Cellular Transformation", *The Journal of Biological Chemistry* 271:(14) 7992–7998, 1996.

Gutman and Wasylk, "Nuclear targets for transcription regulation by oncogenes," *TIG*, 7:49–54, 1991.

Higashino, et al., "ETS–related protein E1A–F can activate three different matrix metalloproteinase gene promoters", *Oncogene* 10:1461–1463, 1995.

Higashino, et al., Isolation of a cDNA encoding the adenovirus E1A enhancer binding protein: a new human member of the ets oncogene family, *Nucleic Acids Research* 21:(3) 547–553, 1993.

International Search Report dated Jul. 8, 1998 (PCT/US98/00880)(UTFC:500P).

Isobe, et al., "Assignment of the ets–Related Transcription Factor E1A–F Gene (ETV4) to Human Chromosone Region 17q21", *Genomics* 28:357–359, 1995.

Macleod, et al., "The ets gene family", *TIBS* 17:251–256, 1992.

O'Hagan, et al., Activation of HER2/neu kinase induces overexpression of the Ets–related transcription factor PEA3, *Proceedings of the American Association for Cancer Research* 37:552, Abstract #3575, 1996.

Scott, et al., An ets related transcription factor contributes to HER2/neu overexpression in human breast cancer cells, *Proceedings of the American Association for Cancer Research* 34:529, Abstract #3158, 1993.

Scott, et al., "Binding of an ETS–related Protein within the DNase I Hypersensitive Site of the HER2/neu Promotor in Human Breast Cancer Cells", *The Journal of Biological Chemistry* 269:(31) 19848–19858, 1994.

Scott, et al., "ETS–related transcription factors isolated from HER2/neu overexpressing breast cancer cells", *Proceedings of the American Association for Cancer Research* 35:598, Abstract #3563, 1994.

Shehin–Johnson, et al., "Identification of Tissue–Specific DNase I Hypersensitive Sites in the Rabbit Flavin–Containing Monooxygenase Form 2 Gene", *Drug Metabolism and Disposition* 24:(8) 891–898, 1996.

Shindoh, et al., "Correlated Expression of Matrix Metalloproteinases and ets Family Transcription Factor E1A–F in Invasive Oral Squamous–Cell–Carcinoma–Derived Cell Lines", *American Journal of Patholoy* 148:(3) 693–700, 1996.

Suzuki, et al., "ETS1 suppress tumorigenicity of human colon cancer cells", *Proc. Nat. Acad. Sci. USA*. 92:4442–4446, 1995.

Trimble, et al., "PEA3 is overexpressed in mouse metastatic mammary adenocarcinomas", *Oncogene* 8:3037–3042, 1993.

Urano, et al., "A Novel Chimera Gene between EWS and E1A–F, Encoding the Adenovirus E1A Enhancer–Binding Protein, in Extraossseous Ewing's Sarcoma", *Biochemical and Biophysical Reaearch Communications* 219:608–612, 1996.

Wasylk et al., "The c–ets proto–oncogenes encode transcription factors that cooperate with c–Fos and C–Jun for transcriptional activation," *Nature*, 346:191–193, 1990.

Xin, et al., Molecular cloning and characterization of PEA3, a new member of the Ets oncogene family that is differentially expressed in mouse embryonic cells, *Genes & Development* 6:481–496, 1992.

Yoshida, et al., "Binding sites of HeLa cell nuclear protein on the upstream region of adenovirus type 5 E1A gene", *Nucleic acids Research* 17:(23) 10015–10035, 1989.*

* cited by examiner

Primary Examiner—Bruce R. Campbell
Assistant Examiner—Richard Schnizer
(74) Attorney, Agent, or Firm—Fulbright & Jaworski L.L.P.

(57) ABSTRACT

The present invention relates generally to the fields of cancer therapy and gene therapy. More particularly, it demonstrates that PEA3 is a tumor suppressor and may be used to treat various forms of cancer, and especially neu–mediated cancer.

14 Claims, 5 Drawing Sheets

PEA3 IS A TUMOR SUPPRESSOR

This is a continuation of co-pending application Ser. No. 08/780,835 filed Jan. 10, 1997, now U.S. Pat. No. 5,922,688.

BACKGROUND OF THE INVENTION

1. Field of the Invention

The present invention relates generally to the fields of cancer therapy and gene therapy. More particularly, it concerns the use of PEA3 to prevent and treat various transformation events.

2. Description of Related Art

It is well established that a variety of cancers are caused, at least in part, by genetic abnormalities that result in either the over-expression of one or more genes, or the expression of an abnormal or mutant gene or genes. For example, in many cases, the expression of oncogenes is known to result in the development of cancer. "Oncogenes" are genetically altered genes whose mutated expression product somehow disrupts normal cellular function or control (Spandidos et al., 1989).

Most oncogenes studied to date have been found to be "activated" as the result of a mutation, often a point mutation, in the coding region of a normal cellular gene, i.e., a "proto-oncogene", that results in amino acid substitutions in the expressed protein product. This altered expression product exhibits an abnormal biological function that takes part in the neoplastic process (Travali et al., 1990). The underlying mutations can arise by various means, such as by chemical mutagenesis or ionizing radiation. A number of oncogenes and oncogene families, including ras, myc, neu, raf erb, src, fis, jun and abl, have now been identified and characterized to varying degrees (Travali et al., 1990; Bishop, 1987).

The neu gene (also known as HER-2/neu or c-erb-2) encodes a 185-kDa transmembrane tyrosine kinase ($p185^{neu}$) with homology to epidermal growth factor receptor (Hung et al., 1986; Coussens et al., 1985; Schechter et al., 1984; Sanba et al., 1985; Yamamoto et al., 1986). Enhanced expression of neu is known to be involved in many human cancers, including NSCLC and has been shown to correlate with poor patient survival in NSCLC (Kern et al., 1990; Schneider et al., 1981; Weiner et al., 1990). Cellular and animal studies have shown that an increase in neu tyrosine kinase activity increases the expression of malignant phenotypes (Muller et al., 1988; Hudziak et al., 1987; Muthuswamy et al., 1994; Yu et al., 1991; Yu el a., 1993; Hung et al., 1989; Sistonen et al., 1989; Yu et al., 1994).

The neu oncogene, was first identified in transfection studies in which NIH 3T3 cells were transfected with DNA from chemically induced rat neuroglioblastomas (Shih et al., 1981). The p185 protein encoded by neu has an extracellular, transmembrane, and intracellular domain, and therefore has a structure consistent with that of a growth factor receptor (Schechter et al., 1984). The human neu gene was first isolated due to its homology with v-erbB and EGF-r probes (Senba et al., 1985).

The neu oncogene plays an important role in carcinogenesis, for example, the gene is amplified in approximately 30% of primary breast cancer. Amplified expressions of the neu oncogene in transfected 3T3 cells induces malignant transformation. neu expression has also been detected in ovarian cancer and its overexpression results in poor prognosis. The expression of neu oncogenes in human tumor cells induce resistance to several host cytotoxic mechanisms.

Along with an increased proliferative potential, neu-mediated cancers appear to be resistant to host defense mechanisms. Studies have shown that overexpression of the neu oncogene in transfected cells results in resistance to tumor necrosis factor, a major effector molecule in macrophage-mediated tumor cell cytotoxicity.

Therefore, neu oncogene expression is correlated with the incidence of cancers of the human breast and female genital tract. Moreover, amplification/overexpression of this gene has been directly correlated with relapse and survival in human breast cancer (Slamon et al., 1987; 1989). Therefore, it is important to evolve information regarding the neu oncogene, particularly information that could be applied to reversing or suppressing the oncogenic progression that seems to be elicited by the presence or activation of this gene. Unfortunately, little has been previously known about the manner in which one may proceed to suppress the oncogenic phenotype associated with the presence of oncogenes such as the neu oncogene.

In addition, neu overexpression in NSCLC is associated with shortened survival. In vitro experimental models have provided evidence that, in the murine cell NIH 3T3, oncogenes increase drug resistance. Furthermore, Tsai et al., 1993 and 1995 used a NSCLC model to demonstrate that activation of an oncogene is quantitatively associated with intrinsic chemoresistance in human malignant cells. This resistance is observed with a variety of drugs that are structurally unrelated and act on different targets and/or by different mechanisms. Thus increased expression of neu oncogene enhances chemoresistance to a wide variety of chemotherapeutic agents (Tsai, 1993) including cisplatin, doxorubicin, and VP16 (Tsai et al., 1993; Tsai et al., 1995). The association of neu overexpression in cancer cells with malignant phenotypes and chemoresistance provides a plausible interpretation for the poor clinical outcome for patients with neu-overexpressing tumors.

Although breast cancer diagnosed in its earliest clinical stages (stage 0, stage Ia) is highly curable, the cure rate for more advanced stages drops precipitously, even after modern combined-modality treatments. Metastatic breast cancer responds to both chemotherapy and hormone therapy, and most patients can be palliated adequately during the 1 to 3 years of usual survival. However, metastatic breast cancer is considered incurable, as demonstrated by the relentless death rates, regardless of the treatment modality utilized. Front-line chemotherapy or hormone therapy programs for correctly selected patients produce objective responses in 50% to 70% of patients, but the median duration of response is usually less than one year. Response rates after second line treatments are considerably lower (20% to 50%), and response durations average 6 months.

Ovarian cancer is also highly curable in its earliest stages, but the overwhelming majority of patients are diagnosed in stages III and IV. Although responsive to chemotherapy, most patients with advanced ovarian cancer relapse and die of their disease. With the introduction of several neu cytotoxic agents (taxanes, vinorelbine, platinum derivatives), some responses are observed after second line therapy too, but cure in this situation remains an elusive goal.

Thus overexpression of the HER-2/neu oncogene correlates with poor survival for breast and ovarian cancer patients and induces metastatic potential and chemoresistance of human cancer cells. Repression of HER-2lneu suppresses the malignant phenotypes of HER-2/neu-overexpressing cancer cells. It suggests that HER-2/neu oncogene is an excellent target for development of novel therapeutic agent for the HER-2/neu-overexpressing cancer cells. Thus methods and compositions that repress HER-2/neu transcription in HER-2/neu-overexpressing human breast and ovarian cancer cell lines, and suppress activated neu induced transformation would be of great therapeutic value in the treatment of these diseases. PEA3, as a transcription factor, targets HER-2/neu gene by repressing its expression, thus it has a great potential to be used as a therapeutic strategy of these neu-mediated cancer types.

In 10–20% of the HER2 overexpressing breast tumors, some gastric and virtually all HER2$^+$ lung cancers HER2 mRNA and protein overexpression occur in the absence of increased gene copy number thus suggesting that HER2 there may be some aberration in transcriptional regulation that plays a fundamental role in the development of these diseased states.

It has been shown that neu transcription can be enhanced by a variety of growth regulatory agents such as phorbol esters, epidermal growth factor and dibutyryl cAMP. Studies with neu promoters have identified cis and trans acting elements that may be involved in the regulation of neu transcription. Many DNA-binding trans-acting proteins are capable of stimulating DNA replication as well as gene transcription. The identification of a specific neu transactivator potentially leads to a molecular understanding of the development of neu gene amplification.

Recent studies showed that there is an ETS response element that is conserved within a Dnase I hypersensitive site in the proximal HER2 promoter region. This study concluded that ETS factors direct the overexpression of many gene products critical for human breast tumorogenesis. In yet another study, it was demonstrated that PEA3, a newly identified member of the ETS family is overexpressed in mouse metastatic mammary adenocarcinoma.

In other, contradictory studies when ETS-1 was ectopically expressed in two different highly tumorogenic human colon cancer cell lines it reversed the transformed phenotype and tumorogenicity in a dose dependent manner (Suzuki et al., 1995). In yet another study raised the question of suppresser activity for some ETS- 1 products in T-cell acute lymphoblastic leukemias.

Hence it appears that there is much confusion regarding the putative role of the ETS family of transcription regulators.

SUMMARY OF THE INVENTION

The present invention generally relates to methods for repressing or preventing transformation in a cell, the method comprising contacting said cell with polyomavirus enhancer activator 3 (PEA3) in an amount effective to inhibit a transformed phenotype. Inhibition of transformation may be indicated by a reduction in a transforming, tumorogenic or metastatic potential of a cell. Such cells may be in cell culture. More preferably, the cell in which transformation is to be repressed are cells in a living organism, for example a human. The inhibition of such transformation has great utility in the prevention and treatment of such transformation-driven events as cancer, tumorigenesis,. and metastasis.

PEA3 is a polypeptide that may be contacted with or introduced to a cell through any of a variety of manners known to those of skill. The PEA3 polypeptide may be introduced through direct introduction of a PEA polypeptide to a cell. In this case, the PEA3 polypeptide may be obtained through any method known in the art, although it is anticipated that in vitro expression of the PEA3 polypeptide in a cell culture system may be a preferred manner of obtaining PEA3.

PEA3 may also be introduced to a cell via the introduction of a nucleic acid that encodes the PEA3 polypeptide to the cell. For example, RNA or DNA encoding PEA3 may be introduced to the cell by any manner known in the art. In certain preferred embodiments, embodiments the PEA3 is introduced into the cell through the introduction of a DNA segment which encodes PEA3. In some such embodiments it is envisioned that the DNA segments will further comprises the PEA3 gene operatively linked to its associated control sequences. For example, the PEA3 gene may be operatively linked to a suitable promoter and a suitable terminator sequence. The construction of such gene/control sequence DNA constructs is well-known within the art. In particular embodiments the promoter is selected from the group consisting of CMV, SV40 IE and RSV LTR. In certain embodiments for introduction, the DNA segment may be located on a vector, for example, a plasmid vector or a viral vector. The viral vector may be, for example, a retroviral vector or an adenoviral vector. Such a DNA segment may be used in a variety of methods related to the invention. The vector may be used to deliver a PEA3 gene to a cell in one of the gene-therapy embodiments of the invention. Also, such vectors can be used to transform cultured cells, and such cultured cells could be used, inter alia, for the expression of PEA3 in vitro.

In some aspects of the invention PEA3 is used to inhibit oncogene-mediated transformation. One particular form of oncogene-mediated transformation against which PEA3 is effective is neu oncogene-mediated transformation. Some preferred embodiments of the present invention take advantage of the inventors' discovery that PEA3 binds to a region in the HER2/neu promoter. In more preferred embodiments the PEA3 binds to a region on the HER2/neu promoter that comprises a sequence of AGGAAG.

In certain aspects of the invention, the PEA3 polypeptide or PEA3-encoding nucleic acid is complexed with a liposome for introduction to a cell. In some embodiments, the liposome comprises one or more of DOTMA, DOPE, or DC-Chol. In some specific embodiments, the liposome comprises DC-Chol. In other embodiments the liposome comprises DC-Chol and DOPE.

In particular embodiments the PEA3 is introduced into a cell that is a human cell.

In many embodiments the cell is a tumor cell. In some presently preferred embodiments the tumor cell is a breast tumor cell or an ovarian tumor cell.

The present invention further provides methods to suppress the growth of an oncogene-mediated tumor in a mammal, the method comprising administering to said tumor a composition comprising PEA3, wherein said administration results in a decrease in the growth rate of said tumor. In some preferred embodiments, the introduction of PEA3 is affected by introduction a nucleic acid encoding PEA3 operatively linked to a promoter wherein the production of the PEA3 results in a decrease in the growth rate of said tumor. In particular embodiments the oncogene-mediated tumor is a neu-mediated tumor. In some preferred aspects of the present invention, the PEA3 or PEA3-encoding nucleic acid is administered in a liposomal complex.

The PEA3 gene products and nucleic acids of the present invention may also be introduced using any suitable method. A "suitable method" of introduction is one that places a PEA3 gene product in a position to inhibit the transformation of a cell. For example, injection, oral, and inhalation methods may be employed, with the skill artisan being able to determine an appropriate method of introduction for a given circumstance. In some preferred embodiments, injection will be used. This injection may be intravenous, intraperitoneal, intramuscular, subcutaneous, intratumoral, intrapleural, or of any other appropriate form.

In certain other aspects of the present invention there are provided therapeutic kits comprising in suitable container, a pharmaceutical formulation of a PEA3 gene product or a nucleic acid encoding a PEA3 gene product. Such a kit may further comprise a pharmaceutical formulation of a therapeutic polypeptide, nucleic acid encoding a therapeutic polypeptide, or chemotherapeutic agent.

In some embodiments of the present invention, the inventor's discovery that PEA is able to inhibit transformation will be used in combination with other anti-transformation/anti-cancer therapies. These other therapies may be known at the time of this application, or may become apparent after the date of this application. PEA3 may be used in combination with other therapeutic polypeptides, nucleic acid encoding other therapeutic polypeptides, or chemotherapeutic agents. For example, PEA3 may be used in conjunction with other known anti-cancer polypeptides, such as P53. PEA3 may be used in conjunction with any known transformation or disease inhibitor. PEA3 may be used with other gene-therapy regimes. PEA3 may be used with any suitable chemotherapeutic drug.

In keeping with long-standing patent law convention, the words "a" and "an," when used in the present specification, including the claims, denote "one or more." Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
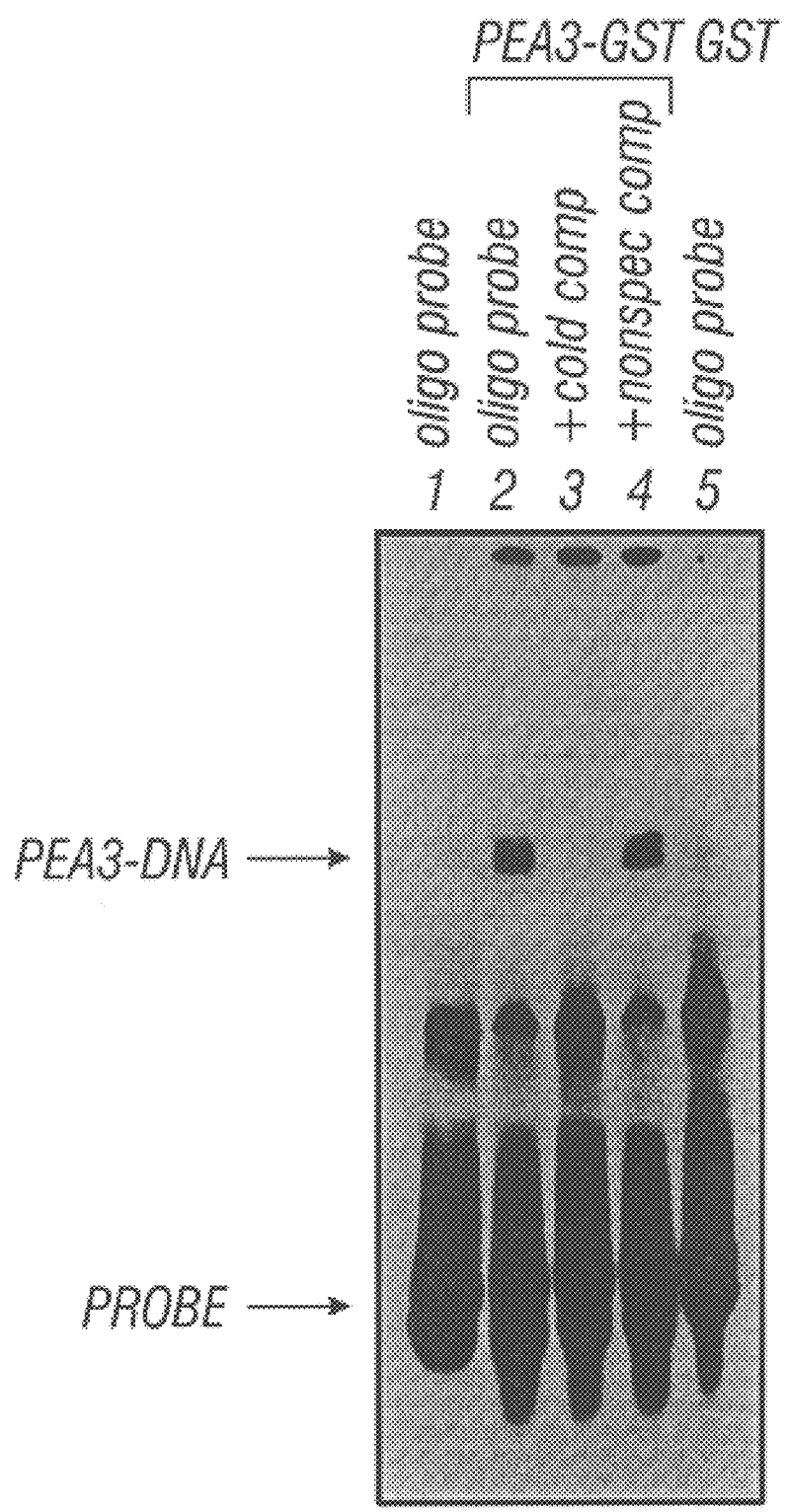
FIG. 1. (Scanned image) Detection of PEA3 protein/DNA complex by gel shift assay.

Radioactivity labeled oligonucleotide probe derived from HER-2/neu promoter was incubated in a binding buffer (lane 1), with 1 $\mu$g of PEA3-GST fusion protein (lane 2). 100 fold molar excess of the same non-radioactivity labeled oligonucleotide was added as specific DNA competitors (lane 3), while addition of 100 fold molar excess of non-specific oliognucleotide as non-specific competitors (lane 4). 1 $\mu$g of GST was incubated with labeled oligonucleotide as a control (lane 5).

Figure 2:
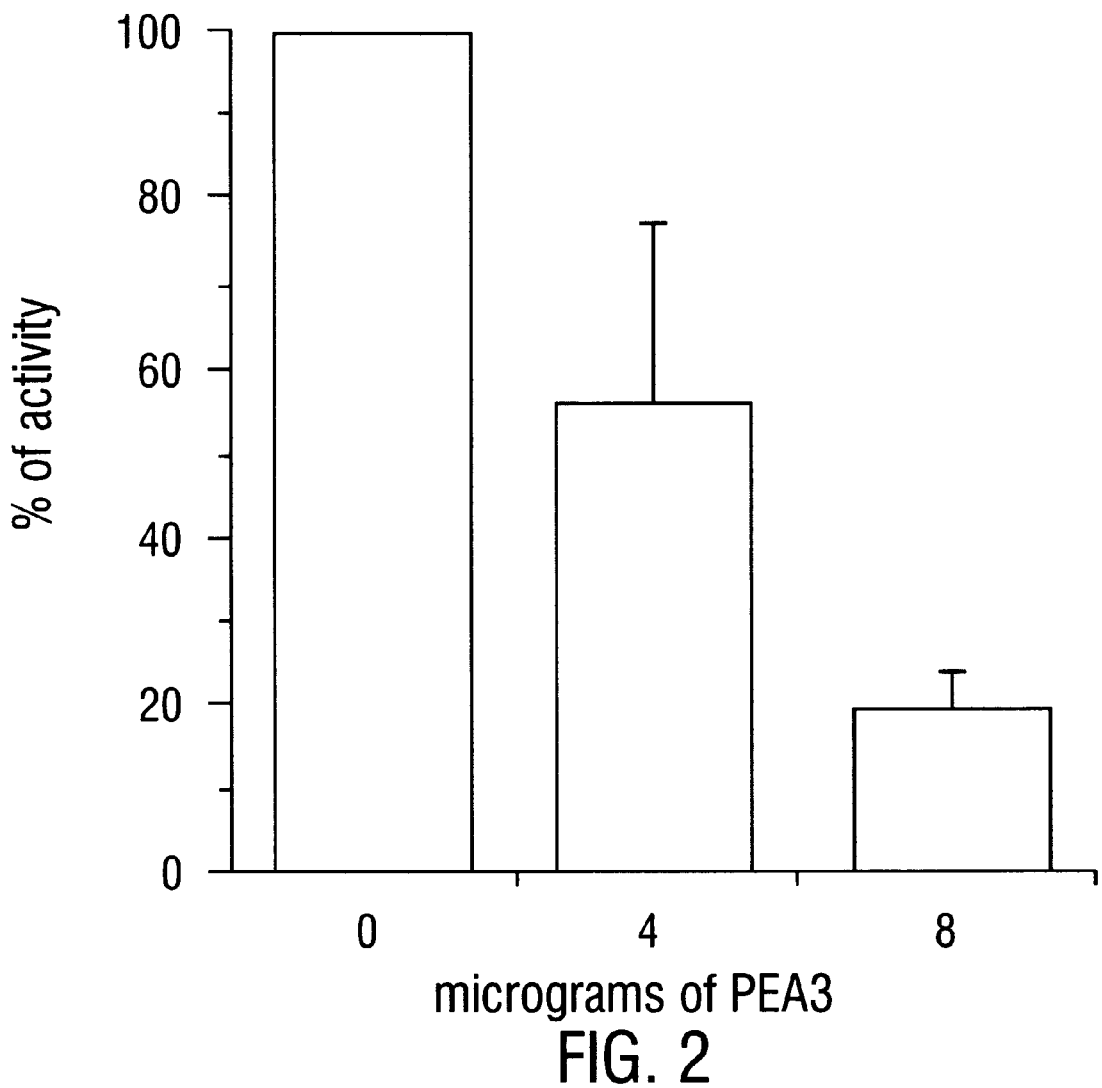

FIG. 2. PEA3 inhibits the HER-2/neu promoter activity in HER-2/neu overexpressing ovarian cancer cell lines. Human ovarian cancer cells, SKOV-3, were cotransfected with 5 $\mu$g pNeulite along with different amounts of PEA3 plasmid DNA as indicated. The luciferase activity of each transfectant was measured. Bar, SD.

Figure 3:
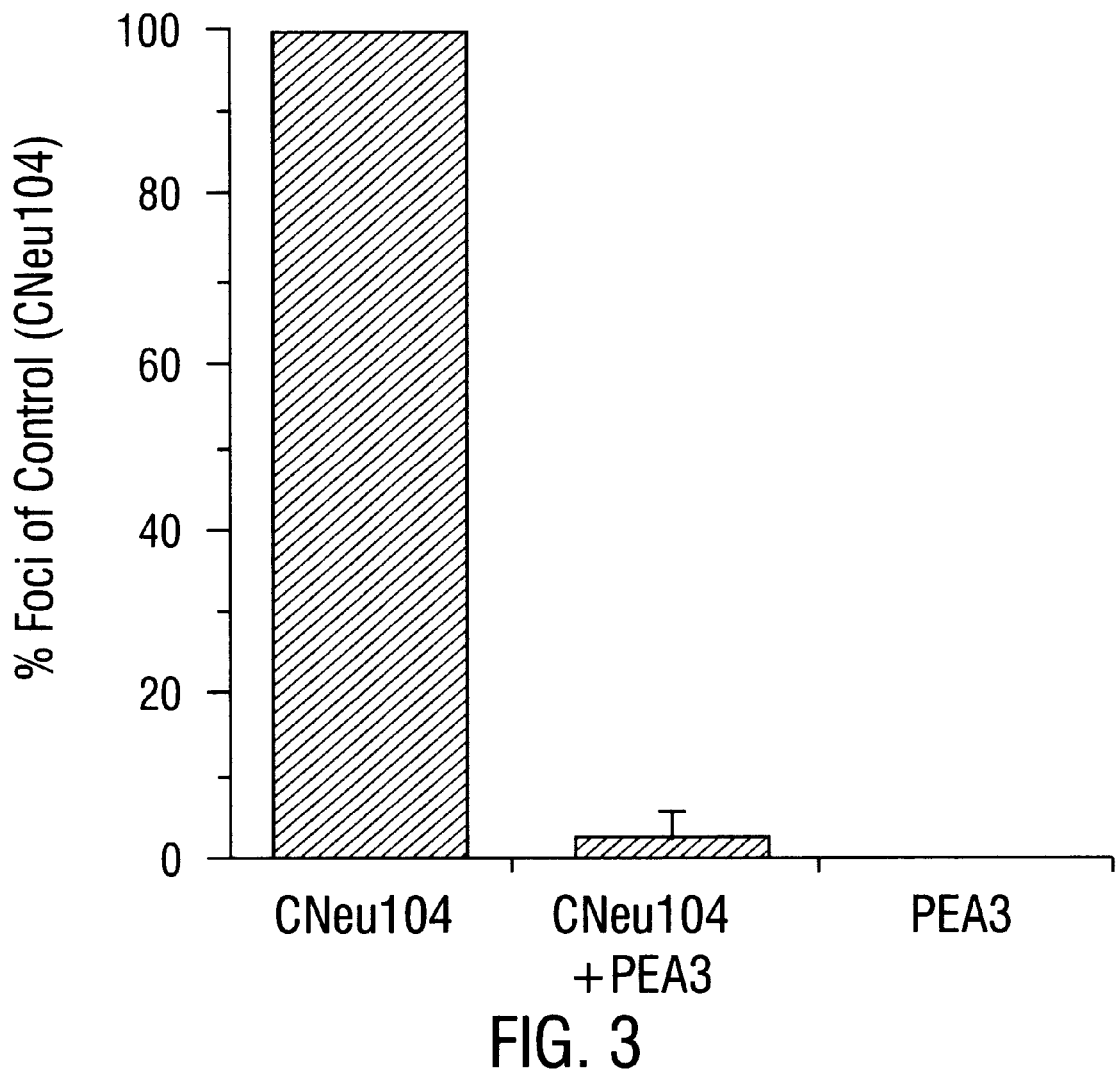

FIG. 3 Repression of the transforming of activated genomic rat neu. CNu104 and/or pSRαPEA3 were cotransfected with pSV2-neo into NIH3T3 mouse fibroblast. Results were expressed as a ratio of foci to colonies from each transfection to normalized transfection-efficiency. The ratio of transfecting cNeul04 alone was set as 100%. Bar: SD.

Figure 4A:
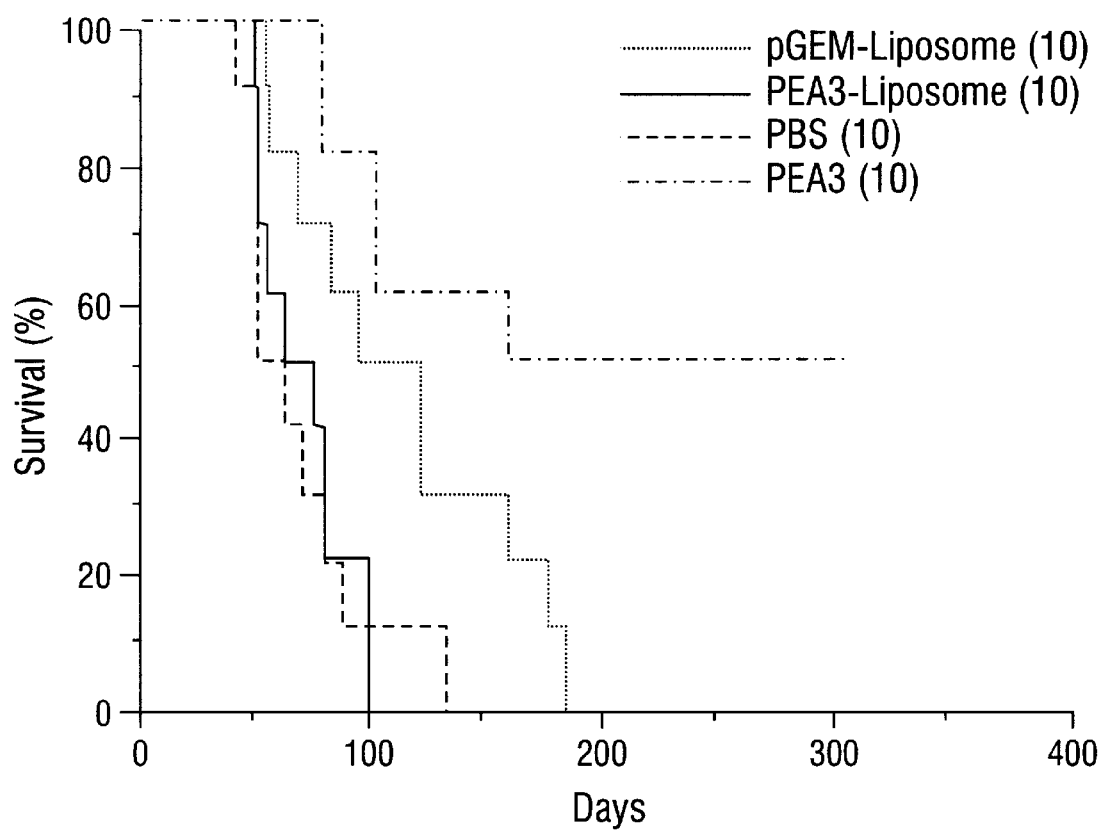
Figure 4B:
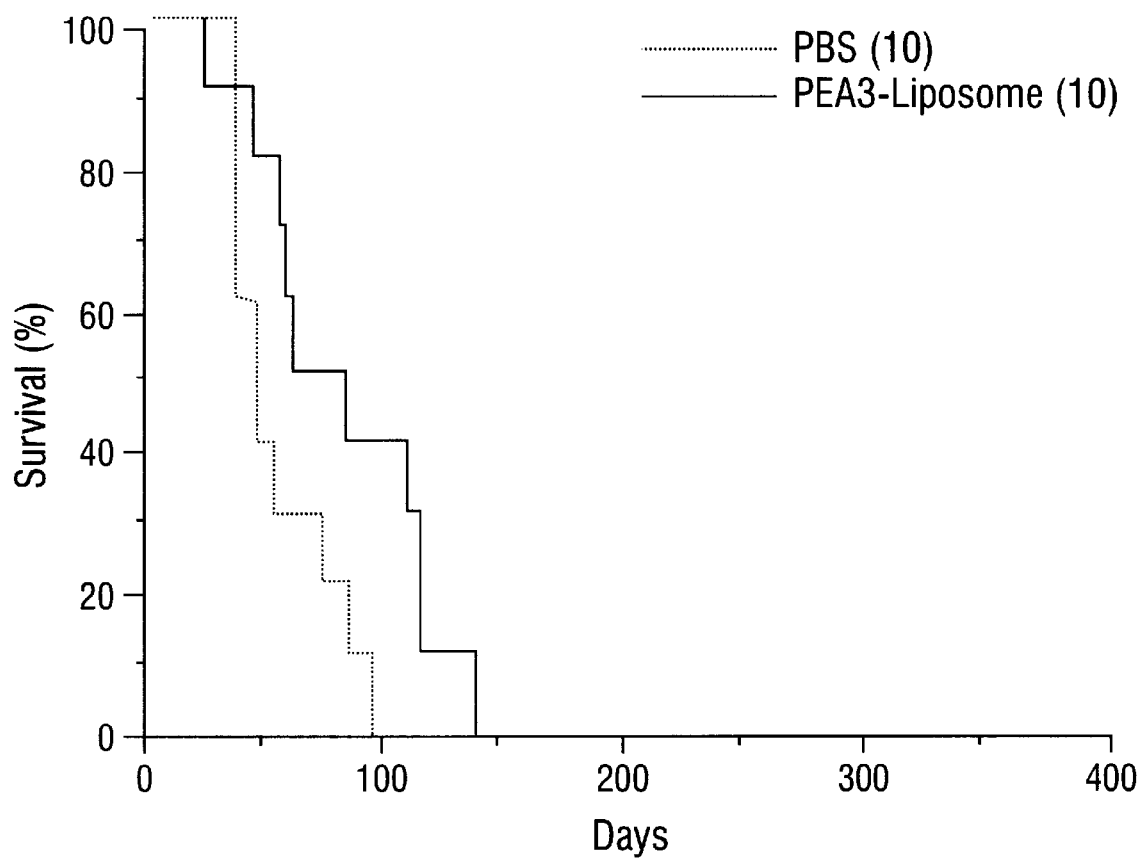

FIG. 4A and FIG. 4B. PEA3-liposome prolonged mice survival specifically in HER-3/neu overexpressing ovarian cancer.

FIG. 4A. Female nu/nu mice were injected i.p. 2×10$^6$ of SKOV-3ipl cells 5 days before treatment. The mice received weekly i.p. injections of 200 $\mu$l of a reagent containing 15 gg control DNA (pGEM) complex with 200 nmol of liposome, 15 $\mu$g of PEA3 DNA, 200 nmol liposome, or PBS. Number of mice in each group is shown in the legend. *marks the last injection.

FIG. 4B. 2774 c-10 cells with basal level of HER-2/neu were inoculated i.p. and treated with PEA3-liposome complex by the same procedure as for SKOV-3.ipl cells.

DESCRIPTION OF ILLUSTRATIVE EMBODIMENTS

Overexpression of the HER-2/neu protooncogene, herein referred to as neu, is found in 20–30% of primary breast cancers and in a similar fraction of human gastric, ovarian and lung adenocarcinoma. The overexpression of this membrane growth factor receptor is associated with HER2 gene amplification, more aggressive tumor growth and a reduced patient survival. In 10–20% of the HER2 overexpressing breast tumors, some gastric and virtually all HER2$^+$ lung cancers HER2 mRNA and protein overexpression occur in the absence of increased gene copy number thus suggesting that HER2 there may be some aberration in transcriptional regulation that plays a fundamental role in the development of these diseased states.

The present inventors have shown that PEA3, a member of the ETS family of transcriptional regulatory factors, regulates HER-2/neu promoter by transcriptional repression. The present invention shows that PEA3 likely functions as a tumor suppressor for HER-2/neu-overexpressing cancer cells and represses HER-2/neu transcription in HER-2/neu-overexpressing human breast and ovarian cancer cell lines, and suppresses activated rat neu induced transformation. By using liposomes as a gene delivery system, the inventors have used PEA3 to successfully retarded the ovarian cancer cell growth and prolonged the survival of mice bearing HER-2/neu-overexpressing ovarian cancers. Methods and compositions for the therapeutic delivery of PEA3 are discussed herein below.

The present invention contemplates the use of PEA3 in reduction of tumor growth in tumors, and employs constructs comprising the ETS domain of PEA3. Although is predicted that PEA3 will play a role in many types of cancer, the present inventors have found that PEA3 constructs are able to inhibit tumorigenicity, especially tumorogenicity of neu-mediated cancer.

The invention further relates to methods of treatment of various types of neu mediated cancers. The PEA3 constructs will be administered in a pharmaceutical composition in therapeutically effective amounts. Those of ordinary skill in the art will readily be able to prepare PEA3 constructs and compositions, as described herein, and to treat cancer in light of the animal model studies detailed herein. It is contemplated that many routes of administration may be utilized in conjunction with the gene constructs and compositions of the invention, such as intravenous injection or even intratumoral instillation as discussed herein below. It is contemplated that the above described methods will be of particular use in regard to neu-mediated cancers.

PEA3 and the ETS family of proteins.

ETS proteins have a conserved DNA-binding domain and regulate transcriptional initiation from a variety of cellular and viral gene promoter and enhancer elements. The first member of the ETS gene family to be discovered was v-ETS, other members include erg, fli-1, elk-1, SAP-1, GABP-α and PEA3 among others, the characteristics of these proteins are shown in Table 1. Some members of the ETS family, ETS-$_1$ and ETS-2, cooperate in transcription with the AP-1 transcription factor, the products of the proto-oncogene families fos and jun while others ELK-1 and SAP-1, form ternary complexes with serum response factor.

TABLE 1

THE ETS GENE FAMILY

| Protein | Source | Molecular mass (kDa) | Amino acid homology to ETS domain of Ets-1 (%) | Human chromosomal location | Expression/features |
|---|---|---|---|---|---|
| Ets-1 | Human mouse chicken | 39–52 63 54/68 | 100 | 11q23 | Elevated expression in thymus and endothelial cells; phosphorylated; alternatively spliced; positively autoregulates transcription |
| Ets-2 | Human chicken | 58/62 | 90 | 21q22 | Expression induced following macrophage differentiation and T-cell activation; alternatively spliced; phosphorylated |
| Erg | Human | 41/52 | 70 | 21q22 | Alternatively spliced; 98% homologous to Fli-1 |
| Fli-1 | Human mouse | 51 | 68 | 11q23 | Activated by proviral insertion of Friend MuLV; 98% homologous to Erg |
| Elk-1 | Human | 60 | 76 | Xp11.2 | ETS domain located in the amino terminus of the protein; forms ternary complex with SRF; shows three regions of homology with SAP-1 |
| SAP-1 a/b | Human | 58/52 | 75 | ND | SRF accessory protein 1, which, like Elk-1, forms a ternary complex with SRF over the c-fos SRE; contains three regions of homology to Elk-1, including the ETS domain, which is located in the amino terminus of the protein; the two isoforms, SAP-1a and SAP-1b, differ in their carboxyl termini |
| Spi-1/PU1 | Human mouse | 30 | 38 | 11p11.22 | Activated in Friend erythroleukaemia by proviral insertion of SFFV; normal expression of the PU-1 transcription factor is restricted to B cells and macrophages |
| E74A/B | Drosophilia | 110/120 | 50 | Drosophilia chromosome 3L74EF | E74A is induced by ecdysone and regulates the expression of E74B, which is also ets-related |
| Elf-1 | Human | 68 | 50 | ND | The ETS domain is the human homologue of the E74A protein of Drosophilia; binds to the NF-AT and NFIL-2B sites in the interleukin-2 promoter and the human immunodeficiency virus 2 LTR |
| GABP-α | Rat | 51 | 82 | ND | High-level expression in rat thymus; complexes with GABP-β, which contains ankyrin repeats, and is related to the Notch protein |
| D-elg | Drosophila | 15 | 64 | Drosophila chromosome 3R97D | Contains only a DNA-binding domain; maternally expressed message and also expressed throughout embryogenesis |
| PEA3 | Mouse | 68 | 63 | ND | Expressed in mouse brain and epididymis and in fibroblast and epithelial cell lines; down-regulated in embryonic cell lines in response to retinoic-acid-induced differentiation |
| TCF1-α | Human | 55 | ND | ND | Very limited homology to ETS domain exists within the HMG box of this factor; expression is restricted to the thymus and is induced following T-cell activation; regulates activity of the TCRα enhancer |

Abbreviations: ND, not determined; MuLV, murine leukaemia virus, SFFV, spleen focus forming virus; SRF, serum response factor; NF-AT, nuclear factor of activating T cells; NFIL-2B, nuclear factor of interleukin 2B; LTR, long terminal repeat; GABP-β, GA-binding protein; PEA3, polyomavirus enhancer activator 3; HGM, high mobility group; TCR, T-cell receptor.

The DNA-binding domain of ETS proteins covers approximately 85 amino acids and is localized at the carboxy terminus of the protein, with the exception of ELK-1, SAP-1 and Elf-1 where it is found at the amino terminus.

PEA3 was initially described as a nuclear protein capable of binding the PEA3 motif in the polymavirus enhancer activator (Martin et al., 1992). The PEA3 gene spans approximately 15 kb and is transcribed to yield a 2.4 kb mRNA capable of encoding a protein (SEQ ID NO:2) with a predicted molecular mass of 61 kDa (Xin et al., 1992). In mice the expression of PEA3 is highly restricted and PEA3 RNA is only detected in the brain and epididymis. PEA3 encoded by the cDNA (SEQ ID NO: 1) binds to the PEA3 motif and activates transcription through this element in HeLa cells strongly suggesting that the PEA3 is a sequence specific transcription activator.

PEA3 DNA binding sites are not restricted to the polyomavirus enhancer and have been located in the promoter regions of many genes that are involved in cell proliferation, migration and metastasis (Wasylyk et al., 1989; Gutman and Wasylyk 1990a and 1990b; Liotta et al., 1991). The transcriptional activity of PEA3 is enhanced by the products of a number of non-nuclear oncogenes including v-src, Ha-ras, u-mos, v-raf, polyomavirus middle T antigen (Wasylyk et al., 1989) and activated neu. It has been noted that neu enhances the transcriptional activity of PEA3 and furthermore neu also induces metastatic tumorogenesis in mammary cells.

p68 ETS-1 protein binds to the PEA3 element of the polyomavirus enhancer (Wasylyk et al., 1990) the DNA sequence AGCAGGAAGT SEQ ID NO:3 is specifically recognized in the polyoma enhancer. Mutational analysis of PEA3 element has identified several higher affinity ETS binding sites such as AGCCGGAAGT SEQ ID NO:4. ETS binding sites have been identified in other viral and cellular regulatory sequences examples of which are given in Table 2.

TABLE 2

REGULATORY ELEMENTS CONTAINING ETS-BINDING SITES

| Regulatory Element | EBS Sequence | Ets Protein Known to Bind |
| --- | --- | --- |
| Ets-2 promoter | TGGAGGAAGT SEQ ID NO:5 | Ets-1/Ets-2 |
| Interleukin 2 enchancer (NF-AT-1) | AAGGAGGAAA SEQ ID NO:6 | Elf-1 |
| Polyomavirus enhancer (PEA3) | AGCAGGAAGT | Ets-1/Ets-2/Erg/Elk-1 |
| Moloney Sarcoma Virus LTR | GAGCGGAAGC SEQ ID NO:7 | Ets-1/Ets-2 |
| SV40 enhancer | AAGAGGAACT SEQ ID NO:8 | PU-1 |
| ICP4 promoter | 6X(CGGAAA/G)[a] | GABP-α: (binding depends on GABP-β) |
| HTLV I LTR | GGAGGAAAT | Ets-1/Ets-2 |
| HTLV I LTR | CCGGGAAGC | Ets-1/Ets-2 |
| Stromelysin 1 promoter | GCAGGAAGC | Ets-1/Ets-2 |
| Stromelysin 1 promoter | CCAGGAAAT | Ets-1/Ets-2 |
| c-fos promoter | CAGGATGT | SAP-1 (binding depends on SRF) |
| T-cell receptor α enhancer | CAGAGGATGT SEQ ID NO:9 | Ets-1 |

Abbreviations: EBS, Ets-binding site; HTLV, human T-cell leukaemia virus.
[a]X = any nucleotide.

Definitions and Techniques Affecting Gene Products and Genes.

PEA3 Gene Products and Genes

In this patent the terms "PEA3 gene product" and "PEA3" refer to proteins having amino acid sequences which are substantially identical to the native PEA3 or which are biologically active in that they are capable of cross-reacting with anti-PEA3 antibody raised against PEA3. "PEA3 gene product" and "PEA3" refer to proteins having amino acid sequences which are substantially identical to the native PEA3 amino acid sequence and which are biologically active in that they are capable of binding to ETS binding sites or cross-reacting with anti-PEA3 antibody raised against PEA3. Such sequences are disclosed, for example, in Macleod et al., (1992). The term "PEA3 gene product" also includes analogs of PEA3 molecules which exhibit at least some biological activity in common with native PEA3. Furthermore, those skilled in the art of mutagenesis will appreciate that other analogs, as yet undisclosed or undiscovered, may be used to construct PEA3 analogs.

The term "PEA3 gene" refers to any DNA sequence that is substantially identical to a DNA sequence encoding an PEA3 gene product as defined above. The term also refers to RNA, or antisense sequences compatible with such DNA sequences. A "PEA3 gene" may also comprise any combination of associated control sequences.

The term "substantially identical", when used to define either a PEA3 amino acid sequence or PEA3 gene nucleic acid sequence, means that a particular subject sequence, for example, a mutant sequence, varies from the sequence of natural PEA3 by one or more substitutions, deletions, or additions, the net effect of which is to retain at least some biological activity of the PEA3 protein. Alternatively, DNA analog sequences are "substantially identical" to specific DNA sequences disclosed herein if: (a) the DNA analog sequence is derived from coding regions of the natural PEA3 gene; or (b) the DNA analog sequence is capable of hybridization of DNA sequences of (a) under moderately stringent conditions and which encode biologically active PEA3; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

Nucleic Acid Sequences

In certain embodiments, the invention concerns the use of neu-suppressing genes and gene products, such as the PEA3 that includes a sequence which is essentially that of the known PEA3 gene, or the corresponding protein. The term "a sequence essentially as PEA3" means that the sequence substantially corresponds to a portion of the PEA3 gene and has relatively few bases or amino acids (whether DNA or protein) which are not identical to those of PEA3 (or a biologically functional equivalent thereof, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of PEA3 will be sequences which are "essentially the same".

PEA3 genes which have functionally equivalent codons are also covered by the invention. The term "functionally equivalent codon" is used herein to refer to codons that encode the same amino acid, such as the six codons for arginine or serine, and also refers to codons that encode biologically equivalent amino acids (Table 3).

TABLE 3

FUNCTIONALLY EQUIVALENT CODONS.

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic Acid | Asp | D | GAC | GAU | | | |
| Glutamic Acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCU | | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein.

Biologically Functional Equivalents

As mentioned above, modification and changes may be made in the structure of PEA3 and still obtain a molecule having like or otherwise desirable characteristics. For example, certain amino acids may be substituted for other amino acids in a protein structure without appreciable loss of interactive binding capacity with structures such as, for example, the neu-gene. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the PEA3 proteins or peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where any changes in the neu-binding region of PEA3 that render the peptide incapable of suppressing neu-mediated transformation would result in a loss of utility of the resulting peptide for the present invention.

Amino acid substitutions, such as those which might be employed in modifying PBA3 are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Sequence Modification Techniques

Modifications to the PEA3 peptides may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the PEA3 gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

Kalderon et al. (1984) report several mutagenic methods which have proved useful in mutating the native LT gene. Specifically, Kalderon et al. teach deletion mutations by displacement-loop mutagenesis and by the random insertion of EcoRI linkers into the LT gene. Further, point mutation by deletion-loop mutagenesis is taught. The reference also teaches screening procedures for determining the success of such mutations. The teachings of Kalderon et al. (1984) are incorporated by reference in this application.

The preparation of sequence variants of the selected gene using site-directed mutagenesis is provided as a means of producing potentially useful PEA3, or other neu-suppressing species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

Other Structural Equivalents

In addition to the PEA3 peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Expression Vectors

In certain aspects of the present invention it may be necessary to express the PEA3 proteins. Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a PEA3 gene and translation of a PEA3 mRNA into a PEA3 protein product. In other embodiments, expression only includes transcription of the nucleic acid encoding a PEA3 or its complement.

In order for the construct to effect expression of at least a PEA3 transcript, the polynucleotide encoding the PEA3 polynucleotide will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a PEA3 polynucleotide is not believed to be critical, so long as it is capable of expressing the polynucleotide in the targeted cell at sufficient levels. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the PEA3 polynucleotide. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of PEA3 polynucleotides. Table 4 lists several elements/promoters which may be employed, in the context of the present invention, to regulate the expression of PEA3 constructs. This list is not intended to be exhaustive of all the possible elements involved in the promotion of PEA3 expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a PEA3 construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 4

| ENHANCER |
|---|
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $α_1$-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV4O |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

Further, selection of a promoter that is regulated in response to specific physiologic signals can permit inducible expression of the PEA3 construct. For example, with the polynucleotide under the control of the human PAI-1 promoter, expression is inducible by tumor necrosis factor. Table 5 illustrates several promoter/inducer combinations:

TABLE 5

| Element | Inducer |
|---|---|
| MT II | Phorbol Ester (TFA) Heavy metals |
| MMTV (mouse mammary tumor virus) | Glucocorticoids |

TABLE 5-continued

| Element | Inducer |
| --- | --- |
| β-Interferon | poly(rI)X |
|  | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV4O Large T Antigen |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding PEA3. Further examples of selectable markers are well known to one of skill in the art.

One typically will include a polyadenylation signal to effect proper polyadenylation of the transcript. The nature of the polyadenylation signal is not believed to be crucial to the successful practice of the invention, and any such sequence may be employed. The inventor has employed the SV40 polyadenylation signal in that it was convenient and known to function well in the target cells employed. Also contemplated as an element of the expression construct is a terminator. These elements can serve to enhance message levels and to minimize read through from the construct into other sequences.

The expression construct may comprise a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series.

In vivo Delivery and Treatment Protocols

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the neu-suppressing gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the PEA3 will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of the PEA3 gene, it is proposed that one will desire to preferably employ a vector construct that will deliver the desired gene to the affected cells. This will, of course, generally require that the construct be delivered to the targeted tumor cells, for example, breast, genital, or lung tumor cells. It is proposed that this may be achieved most preferably by introduction of the desired gene through the use of a viral or non viral vectors to carry the PEA3 sequences to efficiently transfect the tumor, or pretumorous tissue. This infection may be achieved preferably by liposomal delivery but may also be via adenoviral, a retroviral, a vaccinia viral vector or adeno-associated virus.

These vectors have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bg 1 I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

(i) Liposomal Transfection

Thus the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

The present invention also provides particularly useful methods for introducing neu-suppressing gene products into cells. One method of in vivo gene transfer which can lead to expression of genes transfected into cells involves the use of liposomes. Liposomes can be used for both in vitro and in vivo transfection. Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, 1982).

The inventors contemplate that neu-suppressing gene products can be introduced into cells using liposome-mediated gene transfer. It is proposed that such constructs can be coupled with liposomes and directly introduced via a catheter, as described by Nabel et al. (1990). By employing these methods, the neu-suppressing gene products can be expressed efficiently at a specific site in vivo, not just the liver and spleen cells which are accessible via intravenous injection. Therefore, this invention also encompasses compositions of DNA constructs encoding a neu-suppressing gene product formulated as a DNA/liposome complex and methods of using such constructs.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3 β[N-(N'N'-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al., 1990, and Gao et al., 1991. The inventors have had particular success with liposomes comprising DC-Chol. More particularly, the inventors have had success with liposomes comprising DC-Chol and DOPE which have been prepared following the teaching of Gao et al., 1991, in the manner described in the Preferred Embodiments Section. The inventors also anticipate utility for liposomes comprised of DOTMA, such as those which are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allow liposome-mediated transfer of DNA complex, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a neu-suppressing gene. The neu-suppressing gene employed in the liposomal complex can be, for example, a PEA3 gene.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

It is proposed that it will ultimately be preferable to employ the smallest region needed to suppress the neu gene so that one is not introducing unnecessary DNA into cells which receive a PEA3 gene construct. Techniques well known to those of skill in the art, such as the use of restriction enzymes, will allow for the generation of small regions of PEA3. The ability of these regions to inhibit neu can easily be determined by the assays reported in the Examples.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

(ii) Adenovirus

Another method for in vivo delivery involves the use of an adenovirus vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

Adenovirus is a particularly suitable gene transfer vector because of its midsized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 m$\mu$ is particularly efficient during the late phase of infection, and all the mRNA's issued from this promoter possess a 5'-tripartite leader (TL) sequence which makes them preferred mRNA's for translation.

In some cases, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

A particular method of introducing the PEA3 to an animal is to introduce a replication-deficient adenovirus containing the PEA3 gene. The replication-deficient construct made by E1B and E3 deletion also avoids the viral reproduction inside the cell and transfer to other cells and infection of other people, which means the viral infection activity is shut down after it infects the target cell. The PEA3 gene is still expressed inside the cells. Also, unlike retrovirus, which can only infect proliferating cells, adenovirus is able to transfer the PEA3 gene into both proliferating and non-proliferating cells. Further, the extrachromosomal location of adenovirus in the infected cells decreases the chance of cellular oncogene activation within the treated animal.

Introduction of the adenovirus containing the neu-suppressing gene product gene into a suitable host is typically done by injecting the virus contained in a buffer.

The nature of the adenovirus vector is not believed to be crucial to the successful practice of the invention. Of course, as discussed above, it is advantageous if the adenovirus vector is replication defective, or at least conditionally defective, The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Adenovirus is easy to grow and manipulate and exhibits broad host range in vitro and in vivo. This group of viruses can be obtained in high titers, e.g., $10^{9-1011}$ plaque-forming units per ml, and they are highly infective. The life cycle of adenovirus does not require integration in to the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotatic inoculation into the brain (Le Gal La Salle et al., 1993).

(iii) Retroviruses

The retroviruses are a group of single-stranded RNA viruses characterized by an ability to convert their RNA to double-stranded DNA to infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed y components is constructed (Mann et al., 1983). When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact ψ sequence from the recombinant virus inserts upstream from the gag, pol, env sequence integrated in the host cell genome. However, neu packaging cell lines are now available that should greatly decrease the likelihood of recombination (Markowitz et al., 1988; Hersdorffer et al., 1990).

One limitation to the use of retrovirus vectors in vivo is the limited ability to produce retroviral vector titers greater than $10^6$ infections U/mL. Titers 10- to 1,000-fold higher are necessary for many in vivo applications.

Several properties of the retrovirus have limited its use in lung cancer treatment (Stratford-Perricaudet and Perricaudet, 1991; (i) Infection by retrovirus depends on host cell division. In human cancer, very few mitotic cells can be found in tumor lesions. (ii) The integration of retrovirus into the host genome may cause adverse effects on target cells, because malignant cells are high in genetic instability. (iii) Retrovirus infection is often limited by a certain host range. (iv) Retrovirus has been associated with many malignancies in both mammals and vertebrates. (v)

The titer of retrovirus, in general, is 100- to 1,000-fold lower than that of adenovirus.

Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Howrich et al., 1990).

With the recognition of defective hepatitis B viruses, neu insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Chang et al., 1991).

Other non-viral vectors

In order to effect expression of sense or antisense gene constructs, the expression construct must be delivered into a cell. This delivery may be accomplished in vitro, as in laboratory procedures for transforming cells lines, or in vivo or ex vivo (see below), as in the treatment of certain disease states. As described above, delivery may be via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984). direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al, 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific.

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

Combined Therapy Protocols

Tumor cell resistance to DNA damaging agents represents a major problem in clinical oncology. The present invention may also be used in combination with conventional therapies to improve the efficacy of chemo- and radiotherapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that PEA3 therapy could be used similarly in conjunction with chemo- or radiotherapeutic intervention.

To kill cells, such as malignant or metastatic cells, using the methods and compositions of the present invention, one would generally contact a "target" cell with a PEA3 composition and at least one DNA damaging agent. These compositions would be provided in a combined amount effective to kill or inhibit proliferation of the cell. This process may involve contacting the cells with the PEA3 composition and the DNA damaging agent(s) or factor(s) at the same time. This may be achieved by contacting the cell with a single composition or pharmacological formulation that includes both agents, or by contacting the cell with two distinct compositions or formulations, at the same time, wherein one composition includes the PEA3 composition and the other includes the DNA damaging agent.

Alternatively, the PEA3 treatment may precede or follow the DNA damaging agent treatment by intervals ranging from minutes to weeks. In embodiments where the DNA damaging factor and PEA3 are applied separately to the cell, one would generally ensure that a significant period of time did not expire between the time of each delivery, such that the DNA damaging agent and PEA3 composition would still be able to exert an advantageously combined effect on the cell. In such instances, it is contemplated that one would contact the cell with both agents within about 6 hours to one week of each other and, more preferably, within about 24–72 hours of each other, with a delay time of only about 48 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the PEA3 or the DNA damaging. agent will be desired. Various combinations may be employed, where PEA3 is "A" and the DNA damaging agent is "B":

| A/B/A | B/A/B | B/B/A | A/A/B | B/B/B/A | B/B/A/B |
| A/A/B/B | A/B/A/B | A/B/B/A | B/B/A/A | B/A/B/A | B/A/A/B |
| A/A/A/B | B/A/A/A | A/B/A/A | A/A/B/A | A/B/B/B | B/A/B/B |

To achieve cell killing, both agents are delivered to a cell in a combined amount effective to kill the cell.

DNA damaging agents or factors are defined herein as any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cis-platin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells with a DNA damaging agent in addition to the PEA3 composition. This may be achieved by irradiating the localized tumor site with DNA damaging radiation such as X-rays, UV-light, γ-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with a PEA3 composition, as described above.

Agents that directly cross-link polynucleotides, specifically DNA, are envisaged and are shown herein, to eventuate DNA damage leading to a synergistic antineoplastic combination. Agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of polynucleotide precursors and subunits also lead to DNA damage. As such a number of polynucleotide precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of DNA damage, or the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the regional delivery of PEA3 compositions to patients with tumors will be a very efficient method for delivering a therapeutically effective gene to counteract the clinical disease. Similarly, the chemo- or radiotherapy may be directed to a particular, affected region of the subject's body. Alternatively, systemic delivery of the PEA3 or the DNA damaging agent may be appropriate in certain circumstances, for example, where extensive metastasis has occurred.

Cytokine therapy also has proven to be an effective partner for combined therapeutic regimens. Various cytokines may be employed in such combined approaches. Examples of cytokines include IL-1$\alpha$, IL-1$\beta$, IL-2, IL-3, IL-4, IL-5, IL-6, IL-7, IL-8, IL-9, IL-10, IL-11, IL-12, IL-13, TGF-$\beta$, GM-CSF, M-CSF, G-CSF, TNF$\alpha$, TNF$\beta$, LAF, TCGF, BCGF, TRF, BAF, BDG, MP, LIF, OSM, TMF, PDGF, IFN-$\alpha$, IFN-$\beta$, IFN-$\gamma$. Cytokines are administered according to standard regimens, as described below, consistent with clinical indications such as the condition of the patient and relative toxicity of the cytokine.

The present invention also contemplates the use of a combination of therapies in the treatment of neu-mediated cancers. In particular, previous studies have shown that E1A and LT gene products results in the chemosensitization of neu-mediated transformation to chemotherapeutic agents. Likewise tyrosine kinase inhibitors such as emodin also chemosensitize such cancers. The present invention contemplates using PEA3 constructs in combination with E1A, LT and emodin like compounds to affect the treatment of neu mediated cancers.

Chemosensitization Of Neu-Overexpressing Cancer Cells To Chemotherapeutics By Adenovirus 5 E1A Previous studies by the inventors have shown that adenoviral E1A will chemosensitize neu-overexpressing cells to chemotherapeutic agents. In many cases neu overexpression is related to chemoresistance. In exemplary studies the effects of taxol, an exemplary chemotherapeutic agent, on cell of growth rat fibroblasts with various neu and E1A expression were grown in varying concentrations of taxol 0.01–100 $\mu$M was examined. The highest inhibition of cell growth was seen in BE1A1.Hy with neu down regulated by E1A in a taxol concentration of 0.1–10 $\mu$M.

These studies demonstrated that E1A-mediated HER-2/neu repression is able to sensitize the response of HER-2/neu-overexpressing cancer cells to chemotherapeutic agents. This phenomenon occurs only to the HER-2/neu-overexpressing cancer cells. When the breast cancer cells in which HER-21neu is not overexpressed (MDA-MB-435), sensitization can not be observed either in MTT assay or clonogenic assay.

Chemosensitization Of Neu-Overexpressing Cancer Cells To Chemotherapeutics By Emodin-Like Tyrosine Kinase Inhibitors Emodin, was first isolated from *polygonum cuspidatum*, has been shown to be an inhibitor of the protein tyrosine kinase p56$^{lck}$ (Jayasuriya et al., 1992). In the present invention, emodin is shown to inhibit neu tyrosine kinase activity and to preferentially repress the transformation ability and growth rate of neu-overexpressing breast cancer cells. Emodin has been reported to be a tyrosine kinase inhibitor that restricts the activity of p56$^{lck}$ kinase by preventing the binding of ATP in vitro (Jayasuriya et al., 1992). Emodin also can inhibit the growth of cancer cells, including lymphocytic leukemia (Kupchan et al., 1976), HL-60 human leukemia cells (Yeh et al., 1988), and ras-transformed human bronchial epithelial cells (Chan et al., 1993), by an unknown mechanism.

The inventors have demonstrated that emodin and emodin-like compounds suppress the tyrosine kinase activity of neu-overexpressing human breast cancer cells, their transforming ability, and induce their differentiation. Further, the inventors find that emodin also suppresses tyrosine phosphorylation of neu in lung cancer cells and preferentially inhibits growth of these cells. Further, they demonstrated that emodin is able to sensitize lung cancer cells that overexpress neu to the chemotherapeutic agents cisplatin, doxorubicin, and VP16. These results suggested that the tyrosine kinase activity of p185$^{neu}$ is required for the chemoresistant phenotype of neu overexpressing cancer cells. Therefore, the invention shows that adding emodin to chemotherapeutic regimens greatly improves their efficacy.

The present invention contemplates the use of PEA3 in gene therapy in combination with emodin-like tyrosine kinase inhibitors in order to suppress the growth of neu-mediated carcinoma. The delivery of emodin-like tyrosine kinase inhibitors to the neu-mediated cancer cells is well within the skill of those in the art. Treatment and delivery protocols are discussed elsewhere in the specification. Likewise the present invention contemplates the use of PEA3 to down regulate neu in combination with E1A and LT products as discussed above in the instant application.

Pharmaceutical Compositions and Routes of Administration

Compositions of the present invention will have an effective amount of a gene for therapeutic administration in combination with an effective amount of a compound (second agent) that is a chemotherapeutic agent as exemplified above. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors of the present invention are advantageously administered in the form of injectable compositions either as liquid solutions or suspensions; solid forms suitable for solution in, or suspension in, liquid prior to injection also may be prepared. These preparations also may be emulsified. A typical compositions for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for inhibiting tumor cell proliferation may be assembled together in a kit. When the components of the kit are provided in one or more liquid solutions, the liquid solution preferably is an aqueous solution, with a sterile aqueous solution being particularly preferred.

For in vivo use, a chemotherapeutic agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the chemotherapeutic drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

Parenteral Administration

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, tfrimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Targeting of cancerous tissues overexpressing neu may be accomplished in any one of a variety of ways. Plasmid vectors and retroviral vectors, adenovirus vectors, and other viral vectors all present means by which to target human cancers. The inventors anticipate particular success for the use of liposomes to target PEA3 genes to cancer cells. In one of the first series of clinical phase to be performed, DNA encoding PEA3 will be complexed with liposomes in the manner described above, and this DNA/liposome complex will be injected into patients with certain forms of cancer, such as breast cancer, intravenous injection can be used to direct the gene to all cells, including those which overexpress neu. Directly injecting the liposome complex into the proximity of a cancer can also provide for targeting of the complex with some forms of cancer. For example, cancers of the ovary can be targeted by injecting the liposome mixture directly into the peritoneal cavity of patients with ovarian cancer. Of course, the potential for liposomes that are selectively taken up by a population of cancerous cells exists, and such liposomes will also be useful for targeting the gene.

Those of skill in the art will recognize that the best treatment regimens for using PEA3 to suppress neu-mediated cancers can be straightforwardly determined. This is not a question of experimentation, but rather one of optimization, which is routinely conducted in the medical arts. The in vivo studies in nude mice provide a starting point from which to begin to optimize the dosage and delivery regimes. The frequency of injection will initially be once a week, as was done in the mice studies. However, this frequency might be optimally adjusted from one day to every two weeks to monthly, depending upon the results obtained from- the initial clinical trials and the needs of a particular patient. Human dosage amounts can initially be determined by extrapolating from the amrount of PEA3 used in mice, approximately 15 $\mu$g of PEA3 DNA per 50 g body weight. Based on this, a 50 kg woman would require treatment with 15 mg of DNA per dose. In certain embodiments it is envisioned that this dosage may vary from between about 100 $\mu$g/50 g body weight to about 5 $\mu$g/g body weight; or from about 90 $\mu$g/50 g body weight to about 10 $\mu$g/g body weight or from about 80 $\mu$g/50 g body weight to about 15 $\mu$g/g body weight; or from about 75 $\mu$g/50 g body weight to about 20 $\mu$g/g body weight; or from about 60 $\mu$g/50 g body weight to about 30 $\mu$g/g body weight about 50 $\mu$g/50 g body weight to about 40 $\mu$g/g body weight. In other embodiments this dose may be about 5, 8, 10 15, or 20 $\mu$g/50 g. Of course, this dosage amount may be adjusted upward or downward, as is routinely done in such treatment protocols, depending on the results of the initial clinical trials and the needs of a particular patient.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Gel Shift Assay

An oligonucleotide probe was derived from HER-2/neu promoter containing PEA3 binding site. The oligos were end-labeled by 32p-$\gamma$ ATP. 1 $\mu$g of GST-PEA3 fusion protein was used to interact with the oligonucleotide alone, or with the presence of 100 fold molar excess of the same oligonucleotide, or with the presence of 100 fold excess of non-specific oligonucleotide. The 1 $\mu$g of GST protein was also incubated with the labeled probe as control.

Transfections and Luciferase Assays

DNA transfections were performed using the calcium phosphate precipitation method. Briefly, $8\times10^5$ SKOV-3 cells were seeded per 100-mm dish; the following day 5 $\mu$g of the pNEUlit luciferase construct and 4, 8 $\mu$g of PEA3 plasmid DNA were transfected. Total DNA was equalized to 20 $\mu$g by control DNA pGEM. Cells were harvested 3 days later, by adding 800 µl 1× Reporter Lysis Buffer per 100-mm dish (Promega, Madison, Wis.). Luciferase activity was measured by mixing 20 µl of the cell extract with 10 µl 2 mM Coenzyme A and 100 µl buffer (30 mM Tricine, 2 mM ATP, 15 mM $MgSO_4$, 10 mM DTT, pH 7.8). One hundred microliters of 1 mM D-luciferin was then injected, and light output was measured for an integration time of 10 s by using the monolight 2010 Luminomoter (Analytical Luminescence Laboratory).

Focus forming assay

Transfection was performed in mouse fibroblast NIH3T3 cells, using the same method as described in previous paragraph. Total amount of DNA was 15 gg including 2.5 µg of cNeu104, 0.5 µg of pSV2neo, 10 µg of PEA3 cDNA or PGEM. Cells were split to 1:4 48 hours after transfection, duplicated plates were subsequently grown in regular medium (DMEM/F12 supplemented with 10% calf serum) or regular medium supplemented with 400 µg/ml G418. After 3 weeks, foci and G418-resistant colonies were stained with 1% of crystal violet and counted. To normalize the transfection efficiency, the number of the foci formed was divided by the number of G418 colonies obtained.

Orthotopic human ovarian cancer model for liposome-mediated in vivo gene transfer study Four to six week old athymic female homozygous nu/nu mice were purchased from Harlan Spargue Dawley, Inc. (Indianapolis, Ind.) and were cared for and used in accordance with institutional guidelines. Mice were housed for 1 to 2 weeks, and each 6 mouse considered healthy was injected with 100 µl of $2 \times 10^6$ SKOV-3.ipl cells i.p. in aseptic conditions.

To test the therapeutic effects of PEA3-liposome complex on human ovarian cancer, the mice that had a tumor 5 days after injection l.p. of $2 \times 10^6$ SKOV-3.ipl cells were placed in six groups. The mice in each group received injections i.p. weekly of 200 µl of a reagent containing 15 µg PEA3 DNA complex with 200 nmol of liposome, 15 µg control DNA (pGEM) complex with 200 nmol of liposome, 15 µg of PEA3 DNA, or PBS. The responses were observed for 1 year. The survival duration of all the mice was recorded.

Immunohistochemical staining

Frozen sections were taken from tumor samples of tumor-bearing mice for histological analysis. After being fixed with formalin and embedded in paraffin, the sections were subjected to routine hematoxylin-eosin staining. p185 protein was detected by using polyclonal antibody (DAKO corporation) as primary antibody, and biotinylated goat anti-rabbit IgG as second antibody, followed by incubation with streptavidin-alkaline phosphatase, and then developed in an phosphatase substrate kit; 1% methylgreen was used as a counterstain. To detect PEA3 protein expression, monoclonal antibody against PEA3 protein (Santa Cruz) biotinylated anti-mouse IgG was used, followed by incubation with ABC reagent (Vector laboratory), and developed in ABC chromogen substrate solution; mayer's hematoxylin was used as a counterstain.

EXAMPLE 2

PEA3 Binds Directly to HER-2/neu Promoter

By searching for protein binding motif, a PEA3 binding site 5' AGGAAG 3' in the HER-2/neu promoter region was identified. Gel shift assay was performed to see if PEA3 protein can bind specifically to HER-2/neu promoter. Oligonucleotide probe was derived form HER-2/neu promoter containing PEA3 binding site. GST-PEA3 fusion protein was used to interact with oligonucleotide, while GST protein was used as control. From this study, GST-PEA3 forms a complex specifically with the probes that can be competed out by its specific competitors, indicating that PEA3 can specifically bind to HER-2/neu promoter (FIG. 1). This result indicates that PEA3 likely plays an important role in regulating of HER-2/neu oncogene expression by acting on the promoter through PEA3 motif.

EXAMPLE 3

Repression of HER-2/neu Transcription in HER-2/neu-overexpressing Ovarian Cancer Cells By PEA3

Since PEA3 binds to a DNA element in HER-2/neu promoter specifically, the inventors further examined the effects of PEA3 on HER-2/neu transcription. In HER-2/neu ovarian cancer cell line SKOV-3, the inventors transient cotransfected different amounts of PEA3-expressing vector with human HER-2/neu promoter linked to luciferase report construct (pNeulite). According to the luciferase activity of each transfectant (FIG. 2), PEA3 can repress HER-2/neu promoter activity in a dose-dependent manner. Thus PEA3 as a transcription factor dramatically represses the activity of human HER-2/neu promoter.

EXAMPLE 4

PEA3 Represses the Transforming Activity of the Activated Genomic Rat neu

In order to see whether the PEA3 repression of HER-2/neu transcription can result in the suppression of transformation caused by HER-2/neu, the inventors carried out focus forming assay in mouse fibroblast NIH3T3. CNu104 is a cosmid with mutation-activated genomic rat neu under its own promoter. By transfection cNu104 transformed NIH3T3 cells and formed foci. The inventors performed cotransfection studies of cNu104 with PEA3 gene. Cells were split to 1:4 48 hours after transfection, duplicated plates were subsequently grown in regular medium (DMEM-F12 supplemented with 10% calf serum) or regular medium supplemented With 400 µg/ml G418. Foci and G418-resistant colonies were stained and counted after 3 weeks. The foci formation was reduced to only 2.75% of control (FIG. 3). Thus PEA3 can suppress transformation caused by mutation-activated rat neu oncogene. It implies that PEA3 mediated neu repression may suppress transformation of human cancer cells, as it does in mouse fibroblast NIH3T3 cells.

EXAMPLE 5

PEA3 Can Prolong Mice Survival in an Orthotopic Ovarian Cancer Model by Directly Targeting HER-2/neu Gene To see whether PEA3 may suppress in vivo tumor development in mice bearing HER-2/neu-overexpressing cancer cells, the inventors used PEA3-liposome to treat the tumor-bearing mice in an orthotopic ovarian cancer animal model. The inventors induced tumor by injecting i.p. 2×10(6) SKOV3.ipl cells in which HER-2/neu is over-expressed. Five days later, the inventors started weekly i.p. injection of 200 µl of PEA3-liposome complex or proper controls. 2774 c-10, another ovarian cancer cell line expressing basal level of HER-2/neu, was used as control cells. The inventors followed the same procedure as in SKOV3.ipl cells, to inoculate i.p. 2774 c-10 cells and treat mice with PEA3-liposome complex.

Survival curves in FIG. 4A and FIG. 4B show that in 2774 c-10 groups, mice treated with either PEA3-liposome or PBS died of malignant tumor and ascites formation within 5 months. In SKOV-3.ipl groups, the mice form control groups died of tumor and ascites within 6 months, however the mice with PEA3-liposome complex treatment had longer survival time than the controls and 50% of the mice are currently alive without visible tumors after 15 months. These results indicate that PEA3 suppresses growth of HER-2/neu-overexpressing ovarian cancer cells and prolongs the survival of mice bearing HER-2/neu-overexpressing tumors. However, it has little effect on ovarian cancers with normal level of HER-2/neu expression, suggesting that PEA3 may be used as a therapeutic agent for HER-2/neu-overexpressing ovarian cancer.

To confirm that the therapeutic effects on ovarian cancer in vivo were due to PEA3 expression and HER-2/neu repression, the inventors did immunohistochemical analyses to the tumor samples from mice after their death. Representative histological sections were taken from treated or control mice with SKOV-3.ipl or 2774 c-10 induced tumors. After being fixed with formalin and paraffin-embedded, p185 protein was detected by using rabbit polyclonal antibody as primary antibody, and biotinylated goat anti-rabbit IgG as second antibody, followed by incubation with streptavidin-alkaline phosphatase, and then developed in an phosphatase substrate kit; 1% methylgreen was used as a counterstain.

The expression of PEA3 was detected using a monoclonal antibody against PEA3 (Santa Cruz) and biotinylated anti-mouse Ig, followed by incubation with ABC reagent (Vector laboratory) and then developed in ABC chromogen substrate solution; mayeris hematoxylin was used as a counterstain.

In one of the tumors derived from PEA3-liposome treated mice, PEA3 protein staining was positive in approximately 30% of cancer cells, while HER-2/neu-encoded p185 protein staining was very weak positive or negative in approximately 50% cells compared to PBS treated cancer cells. In tumor samples of 2774 c-10 group, which were treated with PEA3-liposome complex, PEA3 protein is expressed in approximately 40% of tumor cells. Since PEA3-liposome complex has no significant therapeutic effects on these mice-bearing 2774 c-10 induced tumors, the tumor suppression function of PEA3 on SKOV-3.ipl cells is most likely through the repression of HER-2/neu-encoded p185 expression.

These results clearly prove the concept that PEA3 is a tumor suppressor, it suppresses HER-2/neu-overexpressing tumor development in an orthotopic ovarian cancer model.

EXAMPLE 6

Human Treatment with PEA3

This example describes a protocol to facilitate the treatment of neu-mediated cancer using PEA3.

A patient presenting a neu-mediated cancer may be treated using the following protocol. neu-overexpression may be detected using the immunohistochemistry methods described below. Patients may, but need not, have received previous chemo- radio- or gene therapeutic treatments. Optimally the patient will exhibit adequate bone marrow function (defined as peripheral absolute granulocyte count of >2,000/mm3 and platelet count of 100, 000/mm3, adequate liver function (bilirubin 1.5 mg/dl) and adequate renal function (creatinine 1.5 mg/dl).

Monitoring neu Overexpression in Tumors

The overexpression of neu is typically monitored before, during, and after the therapy. The following assay may be used to monitor neu-overexpression. Sections of 3- to 4 mm thickness of the primary tumors and of the cell block preparations are cut, deparaffinized in xylene, and rehydrated in descending grades (100–70%) of ethanol. Endogenous peroxidase activity is blocked with 3% hydrogen peroxide in methanol. After several washes in distilled water and phosphate-buffered saline, the sections are incubated with a 1:10 dilution of normal horse serum to minimize background staining. This is followed by incubation for 1 hr at room temperature with the primary antibody (Ab-3 monoclonal antibody, Oncogene Sciences, Uniondale, N.Y.; 1: 100). The peroxidase staining procedure utilizes ABC Elite Kits (Vector Laboratories, Burlingame, Calif.). The immunostaining reactions are visualized using 3-amino-9-ethylcarbazole as the chromogen. The sections and/or cytospin preparations are stained with toluidine blue and mounted in permount. Positive and negative control immunostains are also prepared.

The sections are reviewed by the pathologist. Two features of the immunoreaction will be recorded using a semi quantitative scale: the relative number of positive cells (0%, <10%, 10–50%, and >50%) and the intensity of the reaction (0–3). The pattern of immunostaining (membranous, cytoplasmic) is recorded separately. A tumor is considered neu positive if any neoplastic cells show cell membrane reactivity. Cytoplasmic staining is considered non-specific. A breast carcinoma known for its strong positive membrane staining will be used as a positive control.

The quantitative measurement of neu immunostaining will be performed using computerized image analysis with the SAMBA 4000 Cell Image Analysis System (Image Products International, Inc., Chantilly, Va.) integrated with a Windows based software. A strong staining tumor tissue section will be used as positive control. The primary antibody will be replaced by an isotype-matched irrelevant antibody to set the negative control threshold, averaging the results from ten fields.

Protocol for the Treatment of neu-Mediated Cancer

A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The PEA3 may be delivered to the patient alone or indeed in combination with other therapies. Where a combination therapy is contemplated, the PEA3 may be administered before, after or concurrently with the other anti-cancer agents.

A typical treatment course may comprise about six doses delivered over a 7 to 21 day period. Upon election by the clinician the regimen may be continued six doses every three weeks or on a less frequent (monthly, bimonthly, quarterly etc.) basis. Of course, these are only exemplary times for treatment, and the skilled practitioner will readily recognize that many other time-courses are possible.

In one embodiment, administration simply entails injection of the therapeutic composition into the tumor. In another embodiment, a catheter is inserted into the site of the tumor and the cavity may be continuously perfused for a desired period of time.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

Of course, the above-described treatment regimes may be altered in accordance with the knowledge gained from clinical trials such as those described in Example 7. Those of skill in the art will be able to take the information disclosed in this specification and optimize treatment regimes based on the clinical trials described in the specification.

EXAMPLE 7

Clinical Trials of the Use of PEA3 in Treating Neu-Mediated Cancer

This example is concerned with the development of human treatment protocols using the PEA3. Such drug treatment will be of use in the clinical treatment of various neu-overexpressing cancers in which transformed or cancerous cells play a role. Such treatment will be particularly useful tools in anti-tumor therapy, for example, in treating patients with ovarian, breast and lung cancers that are mediated by neu overexpression and resistant to conventional chemotherapeutic regimens.

The various elements of conducting a clinical trial, including patient treatment and monitoring, will be known to those of skill in the art in light of the present disclosure. The following information is being presented as a general guideline for use in establishing PEA3 in clinical trials.

Patients with advanced, metastatic breast and/or epithelial ovarian carcinoma chosen for clinical study will typically have failed to respond to at least one course of conventional therapy. Measurable disease is not required, however the patient must have easily accessible pleural effusion and/or ascites. Further the patients must carry tumors that overexpress neu oncoprotein. Overexpression may be defined as grade 2 or 3 staining by immunohistochemistry as described above. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the PEA3 and/or other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, p185) and in the cells (PEA3, p185) may be assessed and recorded.

In the same procedure, PEA3 may be administered alone or in combination with the another chemotherapeutic agent. The administration may be in the pleural/peritoneal cavity, directly into the tumor, or in a systemic manner. The starting dose may be 0.5 mg/kg body weight. Three patients may be treated at each dose level in the absence of grade >3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of PEA3 and the lot of anti-cancer drug exceed 5 EU/kg for any given patient.

The PEA3 and/or anti-cancer agent combination may be administered over a short infusion time or at a steady rate of infusion over a 7 to 21 day period. The PEA3 infusion may be administered alone or in combination with the anti-cancer drug and/or emodin like tyrosine kinase inhibitor. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of PEA3 in combination with an anti-cancer drug will be administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12-100 (liver and renal function tests), coagulation profile, and any other appropriate chemistry studies to determine the extent of disease, or determine the cause of exisung symptoms. Also appropriate biological markers in serum should be monitored e.g. CEA, CA 15-3, p185 for breast cancer, and CA 125, p185 for ovarian cancer.

To monitor disease course and evaluate the anti-tumor responses, it is contemplated that the patients should be examined for appropriate tumor markers every 4 weeks, if initially abnormal. with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, p185) and in the cells (p185) may be assessed. For an example of an evaluation profile, see Table 4. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

TABLE 4

EVALUATIONS BEFORE AND DURING THERAPY

| EVALUATIONS | PRE-STUDY | TWICE WEEKLY | WEEKLY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | X[1] | X | | |
| Differential | X | X[1] | X | | |
| Platelet Count | X | X[1] | X | | |
| SMA12-100 (SGPT, Alkaline Phosphatase, Bilirubin, Alb/Total Protein) | X | | | X | |
| Coagulation Profile | X | | | X | |
| Serum Tumor markers (CEA, CA15-3, CA-125, Her-2/neu) | X | | | X[3] | |
| Urinalysis | X | | | X | |
| X-rays: | | | | | |
| chest | X | | X[4] | | |
| others | X | | | | X |
| Pleural/Peritoneal Fluids: (cellularity, cytology, LDH, tumor markers, E1A, HBR-2/neu) | X | | X[5] | X | |
| Spirometry and DLCO | X | | | X[6] | X[6] |

[1]For the first 4 weeks, then weekly, if no myelosuppression is observed.
[2]As indicated by the patient's condition.
[3]Repeated every 4 weeks if initially abnormal.
[4]For patients with pleural effusion, chest X-rays may be performed at 72 hours after first dose then prior to each treatment administration.
[5]Fluids may be assessed 72 hours after the first dose, weekly for the first two courses and then every 4 weeks thereafter.
[6]Four and eight weeks after initiation of therapy.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adelman et al. (1983) DNA 2:183.
Baichwal and Sugden, In: Kucherlapati R, ed. *Gene Transfer.* New York: Plenum Press, pp. 117–148, 1986.
Chan et al., *Biocherm. Biophys. Res. Commun.,* 193:1152–1158, 1993.
Chang et al., *Hepatology,* 14:124A, 1991.
Chen and Okayama, *Mol. Cell Biol.,* 7:2745–2752, 1987.
Coffin, In: Virology, Fields et al. (eds.), New York: Raven Press, pp. 1437–1500, 1990.
Couch et al., *Am. Rev. Resp. Dis.,* 88:394–403, 1963.
Coupar et al., *Gene,* 68:1–10, 1988.
Crea et al. (1978), *Proc. Natl. Acad. Sci. USA* 75:5765.
Culver et al., *Science,* 256:1550–1552, 1992.
Dubensky et al., *Proc. Nat'l Acad. Sci USA,* 81:7529–7533, 1984.
Eichenlaub, R. (1979), *J. Bacteriol* 138:559–566.
Fechheimer et al., *Proc. Nat'l Acad Sci USA,* 84:8463–8467, 1987.
Ferkol etal., *FASEB J,* 7:1081–1091, 1993.
Fraley et al., *Proc. Nat'l Acad. Sci. USA,* 76:3348–3352, 1979.
Friedmann, *Science,* 244:1275–1281, 1989.
Gao et al., (1991), *Biochemical and Biophysical Research Communications,* 179(1):280–285.
Gomez-Foix et al., *J. Biol. Chem.,* 267:25129–25134, 1992.
Gopal, *Mol. Cell Biol.,* 5:1188–1190, 1985.
Graham and Prevec, *Biotechnology,* 20:363–390, 1992.
Graham and van der Eb, *Virology,* 52:456–467, 1973.
Gribskov et al. (1986), *Nucl. Acids Res.,* 14:6745.
Grunhaus and Horwitz, *Seminar in Virology,* 3:237–252, 1992.
Gutman & Wasylyk *EMBO J.* 9 2241–2246, 1990a.
Gutman & Wasylyk Trends Genet., 7, 49–54, 1990b.
Harland and Weintraub, *J. Cell Biol.,* 101: 1094–1099, 1985.
Hermonat and Muzycska, *Proc. Nat'l Acad Sci. USA,* 81:6466–6470, 1984.
Hersdorffer et al., *DNA Cell Biol.,* 9:713–723, 1990.
Herz and Gerard, *Proc. Nat'l Acad Sci. USA* 90:2812–2816, 1993.
Horwich et al., *J. Virol.,* 64:642–650, 1990.
Hudziak et al., *Proc. Natl. Acad. Sci. USA,* 84:7159–7163, 1987.
Hung et al., *Proc. Natl. Acad. Sci. USA,* 86:2545–2548, 1989.
Jayasuriya et al, *J. Nat. Prod,* 55:696–698, 1992.

Kalderon et al. (1984),*Virology,* 139:109–137.
Kaneda et al., *Science,* 243:375–378, 1989.
Kato et al., *J. Biol. Chem.,* 266:3361–3364, 1991.
Kern et al., *Cancer Res.,* 50:5184–5191, 1990.
Klein et al., *Nature,* 327:70–73, 1987.
Kupchan and Karim, *Lloydia,* 39:223–224, 1976.
Le Gal La Salle et al., *Science,* 259:988–990, 1993.
Levrero et al., *Gene,* 101: 195–202, 1991.
Liotta et al *Cell,* 64: 327–336, 1991.
Macleod et al., *Trends Biochem. Sci.* 17, 251–256, 1992.
Mann et al., *Cell,* 33:153–159, 1983.
Markowitz etal., *J. Virol.,* 62:1120–1124, 1988.
Martin et al., *Mol. Cell. Biol.,* 12, 2213–2221, 1992.
Messing et al. (1981) *Third Cleveland Symposium on Macromolecules and Recombinant DNA,* Editor A. Walton, Elsevier, Amsterdam.
Muller, W. J., et al., *Cell,* 54: 105–115, 1988.
Muthuswamy et al., *Mol. Cell. Biol.,* 14:735–743, 1994.
Nabel et al. (1990), Science, 249:1285–1288.
Needleman et al. (1970), *J. Mol. Biol.,* 48:443.
Nicolas & Rubenstein, In: Vectors: *A survey of molecular cloning vectors and their uses,* Rodriguez & Denhardt (eds.), Stoneham: Butterworth, pp. 493–513, 1988.
Nicolau and Sene, *Biochem. Biophys. Acta,* 721:185–190, 1982.
Nicolau et al. (1987), *Methods in Enzymology,* 149:157–176.
Paskind et al., *Virology,* 67:242–248, 1975.
Perales et al., *Proc. Natl. Acad. Sci. USA,* 91:4086–4090, 1994.
Potter et al., "*Proc. Nat'l Acad. Sci. USA,* 81:7161–7165, 1984.
Ragot et al., *Nature,* 361:647–650, 1993.
Renan, *Radiother. Oncol.,* 19:197–218, 1990.
Rich et al., *Hum. Gene Ther.,* 4:461–476, 1993.
Ridgeway, In. Rodriguez R L, Denhardt D T, ed. Vectors: *A survey of molecular cloning vectors and their uses. Stoneham: Butterworth,* pp. 467–492, 1988.
Rippe et al., *Mol. Cell Biol.,* 10:689–695, 1990.
Rosenfeld et al., *Cell,* 68:143–155, 1992.
Rosenfeld et al., *Science,* 252:431–434, 199 1.
Roux et al., *Proc. Natl. Acad Sci. USA,* 86:9079–9083, 1989.
Sam brook et al., *Molecular Cloning: A Laboratory Manual,* 2d Ed., Cold Spring Harbor Laboratory Press, Cold Spring Harbor, N.Y., 1989.
Schechter et al., *Nature,* 312:513–516, 1984.
Schneider et al., *Cancer Res.,* 49:4968–4971, 1981.
Schwartz et al., eds. (1979), *Atlas of Protein Sequence and*
Senba et al. (1985), *Proc. Natl. Acad. Sci. USA,* 82:6497.
Shih et al. (1981), *Nature (London),* 290:261–264.
Sistonen et al., *J. Cell. Biol.,* 109:1911–1919, 1989.
Slamon, D. J., et al., *Science* (Washington DC), 244: 707–712, 1989.
Slamon, et al., *Science,* 240:177–182, 1987.
Smith et al. (1981), *Adv. Appl. Math.,* 2:482.
Spandidos et al., *J. Pathol.,* 157:1–10, 1989.
Stratford-Perricaudet and Perricaudetp. 51–61, In: *Human Gene Transfer,* Eds, O. Cohen-Haguenauer and M. Boiron, Editions John Libbey Eurotext, France, 1991.
Stratford-Perricaudet et al., *Hum. Gene Ther.,* 1:241–256, 1990.
Suzuki et al., *Proce. Nat'l. Acdad. Sci.* 92(10): 4442–4446, 1995.
Temin, In: *Gene Transfer,* Kucherlapati (ed.), New York: Plenum Press, pp. 149–188, 1986.
Top et al., *J. Infect. Dis.,* 124:155–160, 1971.
Travali et al., *FASEB,* 4:3209–3214, 1990.
Tsai et al., *J. Natl. Cancer Inst.,* 85:897–901, 1993.
Tsai, C. M., et al., *J. Natl. Cancer Inst.,* 87: 682–684, 1995.
Tur-Kaspa et al., *Mol. Cell Biol.,* 6:716–718, 1986.
Varmus et al., *Cell,* 25:23–36, 1981.
Wagner et al., *Science,* 260:1510–1513, 1990.
Wasylyk et al., *EMBO J.,* 8:3371–3378, 1989.
Wasylyk et al., Nature 346, 191–193, 1990.
Weiner, D. B., et al., *Cancer Res.,* 50: 421–425, 1990.
Wu and Wu, *Biochemistry,* 27:887–892, 1988.
Wu and Wu, *J. Biol. Chem.,* 262:4429–4432, 1987.
Xin et al., *Genes & Develop.* 6, 481–496, 1992.
Yamrnamoto et al., *Cancer Res.,* 46:414–416, 1986.
Yang et al., *Proc. Natl. Acad Sci. USA,* 87:9568–9572, 1990.
Yeh et al., *Planta Med.,* 54:413–414, 1988.
Yu, D. and Hung, M. C. *Oncogene,* 6:1991–1996,1991.
Yu, D., et al., *Cancer Res.,* 53: 891–898, 1993.
Yu, D., et al., *Cancer Res.,* 54: 3260–3266, 1994.
Zelenin et al., *FEBS Lett.,* 280:94–96, 1991.

---

What is claimed is:

1. A pharmaceutical composition comprising a nucleic acid encoding a polyomavirus enhancer activator 3 (PEA3) gene product operatively linked to control sequences wherein the nucleic acid is adapted for use in the treatment of a mammal.

2. The composition of claim 1, wherein said nucleic acid encoding a PEA3 gene product is complexed with a lipid.

3. The composition of claim 2, wherein said lipid comprises DOTMA, DOPE, or DC-Choi.

4. The composition of claim 3, wherein the lipid comprises DC-Chol.

5. The composition of claim 3, wherein the lipid comprises DC-Chol and DOPE.

6. The composition of claim 2, further comprising hemagglutining virus.

7. The composition of claim 2, further comprising nuclear non-histone chromosomal protein.

8. At The composition of claim 1, wherein said nucleic acid encoding a PEA3 gene product is located on a vector.

9. The composition of claim 8, wherein said vector comprises a plasmid vector.

10. The composition of claim 8, wherein said vector comprises a viral vector.

11. The composition of claim 10, wherein the viral vector is selected from the group consisting of an adenoviral vector, a retroviral vector, a vaccinia viral vector, and an adeno-associated viral vector.

12. The composition of claim 1, wherein said nucleic acid encoding a PEA3 gene product is operably linked to a promoter.

13. The composition of claim 1, wherein said promoter is selected from the group consisting of polyoma, ctyomegalovirus, adenovirus 2 and SV40.

14. The composition of claim 1, further comprising a cell-receptor specific ligand.

* * * * *

UNITED STATES PATENT AND TRADEMARK OFFICE
CERTIFICATE OF CORRECTION

PATENT NO. : 6,172,212 B1
DATED : January 9, 2001
INVENTOR(S) : Hung et al.

It is certified that error appears in the above-identified patent and that said Letters Patent is hereby corrected as shown below:

Column 49, claim 3,
Line 50, please delete "DC-Choi" and insert -- DC-Chol -- therefor.

Column 49, claim 8,
Line 59, please delete "At" before "The" therefor.

Signed and Sealed this

Fifteenth Day of January, 2002

Attest:

JAMES E. ROGAN
Attesting Officer
Director of the United States Patent and Trademark Office

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
       (A) LENGTH: 2410 base pairs
       (B) TYPE: nucleic acid
       (C) STRANDEDNESS: single
       (D) TOPOLOGY: linear (xi) SEQUENCE DESCRIPTION: SEQ ID NO: 1:

```
GAATTCCGTG GATGTGCTTT AAAACCACAC CTAACGTTTG AGCACAAGTC TCACGAACTG      60

GCGCTACAAC TTCATCAGAA ACGAAGTCTC CAAATCTGTC CAACGCAAAA ACACAAAGGA     120

GTCTAATGAC TAAGTCTTCC AACCACAACT GTCTGCTGCG CCCGGAAAAC AAGCCGGGGC     180

TCTGGGGACC CGGGGCTCAG GCCGCCTCGC TCCGGCCTAG CCCCGCCACC TTAGTTGTGT     240
```

-continued

```
CATCCCCCGG GCATGCTGAG CATCCCCCCG CGGCTCCGGC ACAGACGCCC GGACCTCAGG      300
TCTCTGCCTC CGCGCGGGGG CCCGGCCCTG TGGCCGGAGG GAGCGGCCGG ATGGAGCGGA      360
GGATGAAAGG CGGATACTTG GACCAGCGAG TGCCCTACAC CTTCTGCAGC AAATCTCCCG      420
GAAATGGGAG CTTGGGCGAA GCGCTGATGG TCCCGCAGGG AAAGCTCATG ACCCGGGCT       480
CCCTGCCGCC TTCCGACTCA GAAGATCTCT TCCAGGACCT CAGTCACTTC AAGAGACGT       540
GGCTCGCAGA AGCTCAGGTA CCGGACAGTG ATGAGCAGTT TGTTCCTGAT TTCCATTCAG      600
AAAACTTAGC TTTCCATAGC CCCACCACCA GGATCAAGAA GGAACCCCAG AGTCCCCGCA      660
CAGACCCCGC CCTGTCCTGC AGCAGGAAGC CACCACTCCC CTACCACCAT GGAGAGCAGT      720
GCCTTTACTC CAGACAAATC GCCATCAAGT CCCCCGCTCC CGGTGCCCCT GGACAGTCGC      780
CCCTGCAGCC CTTTTCCAGG GCAGAACAGC AGCAGAGCCT CCTGAGAGCC TCCAGCTCTT      840
CCCAGTCCCA CCCTGGCCAC GGGTACCTTG GTGAGCACAC CTCCGTCTTC CAGCAGCCCG      900
TGGACATGTG CCACTCCTTC ACATCTCCTC AGGGAGGGGG CCGGGAACCT CTCCCAGCCC      960
CCTATCAACA CCAACTGTCG GAGCCCTGCC CACCCTACCC CCAGCAGAAC TTCAAGCAGG     1020
AGTACCATGA CCCCCTGTAC GAACAGGCTG GCCAGCCCGC TTCAAGCCAG GGTGGGGTCA     1080
GTGGGCACAG GTACCCAGGG GCGGGGGTGG TGATCAAACA GGAGCGCACA GACTTCGCCT     1140
ACGACTCAGA TGTCCCTGGA TGTGCATCAA TGTACCTCCA CCCAGAGGGC TTCTCTGGAC     1200
CCTCTCCAGG TGATGGAGTG ATGGGTTATG CTATGAAAA ATCCCTTCGA CCATTCCCAG      1260
ATGATGTCTG CATTGTCCCT AAAAAATTTG AAGGAGACAT CAAGCAGGAA GGGATTGGAG     1320
CTTTCCGGGA GGGGCCACCC TACCAGCGCC GGGGTGCCTT ACAACTGTGG CAGTTTCTGG     1380
TGGCCCTGCT GGATGACCCA ACAAATGCTC ATTTCATTGC TTGGACAGGC CGGGGAATGG     1440
AGTTTAAACT AATTGAACCT GAAGAGGTTG CCAGGCTCTG GGGTATCCAG AAGAACCGGC     1500
CAGCCATGAA TTATGACAAG CTGAGCCGCT CGCTGCGATA CTATTATGAG AAAGGCATCA     1560
TGCAGAAGGT GGCTGGCGAA CGCTACGTGT ACAAGTTTGT GTGCGAGCCG GAGGCCCTGT     1620
TCTCTCTGGC CTTCCCAGAT AATCAACGTC CAGCTCTGAA GGCTGAGTTT GACCGGCCAG     1680
TCAGTGAGGA GGACACAGTC CCTTTGTCCC ACTTGGATGA GAGTCCTGCC TACCTCCCAG     1740
AACTCACTGG CCCCGCTCCG CCCTTCGGCC ACAGAGGTGG ATATTCTTAC TAGGCACCAG     1800
TGGCTTCCCC TTGACATGGT GGGGTTGCTC AGTGTATATA TCAACTGATT TGGTATTGGT     1860
GAAGGCCCTC TTTCTGATGC CTGTAGAAGT CTCTGGGGTC AGAGCTCCAC TATCCCATCT     1920
GATACTCCTG GCCAGACTCA GCTGCTAACC AGAGTCTGCG GGAAAGACAG TGGAGGCAGG     1980
CCAAATCTAA AGGCAGTAGC TGAAGTTCGC TGTGGCTCAC CTGTACCTTC AGTTCAGCTT     2040
GGCCTCTGCC TAGGTCTTGC TCAGAGGCCA AGTTCCTCAC CCCCACCACA GAGATCCAGT     2100
GTTCTATTCT GGGGACATAC AGGGACTTCC CTTGTTTATT ATGGCAACAG GGCCAAGGGG    2160
ATTCTCAGAA CACCCTGTGT CTCCCCTCTC CCAACCCCCC ATGGGAGACA AAGTTCTGCC     2220
TGGCTTCTGC CCTGAACAGG GGGGTCCTGT GTTCTTGGTG CTGTGCTCTG GGAGGCAGGA    2280
GCATGTGGGC GGCAGCTGGG GGGGGTGTG GAAGTAGAGA TGGCTCTCTG CCCTAGGCCT     2340
ACCCAGGCCT AATTCCACCT TTGCCTCTTA TGCCAGACCT AATAAAGCC TCTGCTTCTC     2400
CCCGGAATTC                                                          2410
```

(2) INFORMATION FOR SEQ ID NO: 2:

(i) SEQUENCE CHARACTERISTICS:

(A) LENGTH: 555 amino acids
(B) TYPE: amino acid
(C) STRANDEDNESS: single
(D) TOPOLOGY: linear (xi) SEQUENCE DESCRIPTION: SEQ ID NO: 2:

```
Met Thr Lys Ser Ser Asn His Asn Cys Leu Leu Arg Pro Glu Asn Lys
1               5                   10                  15

Pro Gly Leu Trp Gly Pro Gly Ala Gln Ala Ala Ser Leu Arg Pro Ser
            20                  25                  30

Pro Ala Thr Leu Val Val Ser Ser Pro Gly His Ala Glu His Pro Pro
        35                  40                  45

Ala Ala Pro Ala Gln Thr Pro Gly Pro Gln Val Ser Ala Ser Ala Arg
50                  55                  60

Gly Pro Gly Pro Val Ala Gly Gly Ser Gly Arg Met Glu Arg Arg Met
65                  70                  75                  80

Lys Gly Gly Tyr Leu Asp Gln Arg Val Pro Tyr Thr Phe Cys Ser Lys
                85                  90                  95

Ser Pro Gly Asn Gly Ser Leu Gly Glu Ala Leu Met Val Pro Gln Gly
            100                 105                 110

Lys Leu Met Asp Pro Gly Ser Leu Pro Pro Ser Asp Ser Glu Asp Leu
        115                 120                 125

Phe Gln Asp Leu Ser His Phe Gln Glu Thr Trp Leu Ala Glu Ala Gln
130                 135                 140

Val Pro Asp Ser Asp Glu Gln Phe Val Pro Asp Phe His Ser Glu Asn
145                 150                 155                 160

Leu Ala Phe His Ser Pro Thr Thr Arg Ile Lys Lys Glu Pro Gln Ser
                165                 170                 175

Pro Arg Thr Asp Pro Ala Leu Ser Cys Ser Arg Lys Pro Pro Leu Pro
            180                 185                 190

Tyr His His Gly Glu Gln Cys Leu Tyr Ser Arg Gln Ile Ala Ile Lys
        195                 200                 205

Ser Pro Ala Pro Gly Ala Pro Gly Gln Ser Pro Leu Gln Pro Phe Ser
210                 215                 220

Arg Ala Glu Gln Gln Gln Ser Leu Leu Arg Ala Ser Ser Ser Ser Gln
225                 230                 235                 240

Ser His Pro Gly His Gly Tyr Leu Gly Glu His Ser Ser Val Phe Gln
                245                 250                 255

Gln Pro Val Asp Met Cys His Ser Phe Thr Ser Pro Gln Gly Gly Gly
            260                 265                 270

Arg Glu Pro Leu Pro Ala Pro Tyr Gln His Gln Leu Ser Glu Pro Cys
        275                 280                 285

Pro Pro Tyr Pro Gln Gln Asn Phe Lys Gln Glu Tyr His Asp Pro Leu
290                 295                 300

Tyr Glu Gln Ala Gly Gln Pro Ala Ser Ser Gln Gly Val Ser Gly
305                 310                 315                 320

His Arg Tyr Pro Gly Ala Gly Val Val Ile Lys Gln Glu Arg Thr Asp
                325                 330                 335

Phe Ala Tyr Asp Ser Asp Val Pro Gly Cys Ala Ser Met Tyr Leu His
            340                 345                 350

Pro Glu Gly Phe Ser Gly Pro Ser Pro Gly Asp Gly Val Met Gly Tyr
        355                 360                 365

Gly Tyr Glu Lys Ser Leu Arg Pro Phe Pro Asp Asp Val Cys Ile Val
370                 375                 380
```

-continued

```
Pro Lys Lys Phe Glu Gly Asp Ile Lys Gln Glu Gly Ile Gly Ala Phe
385                 390                 395                 400

Arg Glu Gly Pro Pro Tyr Gln Arg Arg Gly Ala Leu Gln Leu Trp Gln
            405                 410                 415

Phe Leu Val Ala Leu Leu Asp Asp Pro Thr Asn Ala His Phe Ile Ala
            420                 425                 430

Trp Thr Gly Arg Gly Met Glu Phe Lys Leu Ile Glu Pro Glu Glu Val
            435                 440                 445

Ala Arg Leu Trp Gly Ile Gln Lys Asn Arg Pro Ala Met Asn Tyr Asp
450                 455                 460

Lys Leu Ser Arg Ser Leu Arg Tyr Tyr Glu Lys Gly Ile Met Gln
465                 470                 475                 480

Lys Val Ala Gly Glu Arg Tyr Val Tyr Lys Phe Val Cys Glu Pro Glu
            485                 490                 495

Ala Leu Phe Ser Leu Ala Phe Pro Asp Asn Gln Arg Pro Ala Leu Lys
            500                 505                 510

Ala Glu Phe Asp Arg Pro Val Ser Glu Glu Asp Thr Val Pro Leu Ser
            515                 520                 525

His Leu Asp Glu Ser Pro Ala Tyr Leu Pro Glu Leu Thr Gly Pro Ala
            530                 535                 540

Pro Pro Phe Gly His Arg Gly Gly Tyr Ser Tyr
545                 550                 555
```

(2) INFORMATION FOR SEQ ID NO: 3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 3:

AGCAGGAAGT          10

(2) INFORMATION FOR SEQ ID NO: 4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 4:

AGCCGGAAGT          10

(2) INFORMATION FOR SEQ ID NO: 5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 5:

TGGAGGAAGT          10

(2) INFORMATION FOR SEQ ID NO: 6:

(i) SEQUENCE CHARACTERISTICS:
        (A) LENGTH: 10 base pairs
        (B) TYPE: nucleic acid
        (C) STRANDEDNESS: single -continued

```
        (D) TOPOLOGY: linear (xi) SEQUENCE DESCRIPTION: SEQ ID NO: 6:

AAGGAGGAAA                                                              10

(2) INFORMATION FOR SEQ ID NO: 7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 7:

GAGCGGAAGC                                                              10

(2) INFORMATION FOR SEQ ID NO: 8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 8:

AAGAGGAACT                                                              10

(2) INFORMATION FOR SEQ ID NO: 9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO: 9:

CAGAGGATGT                                                              10
```